US007550266B2

(12) United States Patent
Slepnev

(10) Patent No.: US 7,550,266 B2
(45) Date of Patent: Jun. 23, 2009

(54) METHODS AND SYSTEMS FOR DYNAMIC GENE EXPRESSION PROFILING

(75) Inventor: Vladimir I. Slepnev, Newton, MA (US)

(73) Assignee: Primera Biosystems, Inc., Mansfield, MA (US)

( * ) Notice: Subject to any disclaimer, the term of this patent is extended or adjusted under 35 U.S.C. 154(b) by 150 days.

(21) Appl. No.: 11/318,278

(22) Filed: Dec. 23, 2005

(65) Prior Publication Data
US 2006/0105380 A1 May 18, 2006

Related U.S. Application Data

(62) Division of application No. 10/113,034, filed on Apr. 1, 2002, now abandoned.

(60) Provisional application No. 60/346,140, filed on Oct. 24, 2001.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.33

(58) Field of Classification Search .................. 435/6, 435/91.2; 536/24.33
See application file for complete search history.

(56) References Cited

U.S. PATENT DOCUMENTS

| | | | |
|---|---|---|---|
| 5,658,764 A | 8/1997 | Pergolizzi et al. | |
| 5,691,136 A | 11/1997 | Lupski et al. | 435/6 |
| 6,005,663 A | 12/1999 | Waterhouse et al. | |
| 6,054,035 A | 4/2000 | Kambara | |
| 6,110,680 A | 8/2000 | Sutcliffe et al. | 435/6 |
| 6,180,349 B1 * | 1/2001 | Ginzinger et al. | 435/6 |
| 6,207,031 B1 | 3/2001 | Adourian et al. | |
| 6,303,308 B1 * | 10/2001 | Halle et al. | 435/6 |
| 6,342,376 B1 * | 1/2002 | Kozian et al. | 435/91.2 |
| 6,482,615 B2 | 11/2002 | Tal et al. | |
| 6,706,476 B1 | 3/2004 | Thirstrup et al. | 435/6 |
| 2002/0146688 A1 | 10/2002 | Kinjo | |
| 2002/0160361 A1 | 10/2002 | Loehrlein et al. | |

FOREIGN PATENT DOCUMENTS

| | | |
|---|---|---|
| DE | 19921419 A1 | 11/2000 |
| DE | 19963857 A1 | 7/2001 |
| WO | WO 9729211 A1 * | 8/1997 |
| WO | 98/33942 A1 | 8/1998 |
| WO | WO 00/35274 A | 6/2000 |
| WO | 00/66995 A2 | 11/2000 |
| WO | 02/016652 A2 | 11/2002 |
| WO | 03035841 | 5/2003 |
| WO | 2004048528 | 6/2004 |

OTHER PUBLICATIONS

Garcia, et al. Journal of Molecular Diagnostics, vol. 7, No. 4 (2005). Scalable transcriptional analysis routine-multiplexed quantitative real-time polymerase chain reaction platform for gene expression analysis and molecular diagnostics.

Myakishev, et al. Genome Research, vol. 11, No. 1 (2001). High-throughput SNP genotyping by allele-specific PCR with universal energy-transfer-labeled primers.

Belgrader, P. and Marino, M.A., LRA, 9:3-7 (1997). "Automated Sample Processing Using Robotics for Genetic Typing of Short Tandem Repeat Polymorphisms by Capillary Electrophoresis."

Rajevic et al. (2001), "Assessment of differential expression of oncogenes in gastric adenocarcinoma by fluorescent multiplex RT-PCR assay," *Eur J Physiol* 442(6 Suppl 1):R190-192.

Borson et al. (1988), "Direct Quantitation of RNA Transcripts by Competitive Single-Tube RT-PCR and Capillary Electrophoresis," *Biotechniques* 25:130-137.

George, et al., (1997), "Capillary electrophoresis methodology for identification of cancer related gene expression patterns of fluorescent differential display polymerase chain reaction," *J Chromatogr B Biomed Sci Appl* 695:93-102.

Odin et al., (1999), "Rapid method for relative gene expression determination in human tissues using automated capillary gel electrophoresis and multicolor detection," *J Chromatogr B Biomed Sci Appl* 734:47-53.

Omori, et al. (2000), "Comparative PCR: A Simple and Sensitive Method for Quantifying Low-Abundance mRNA Species," *Genomics* 67:140-145.

Ohtsuki, et al. (2001), "Unnatural base pairs for specific transcription," *PNAS* 98:4922-4925.

Matzl, et al., *Ordered differential display: a simple method for systematic comparison of gene expression profiles*, 1997 Oxford University Press, Nucleic Acids Research, 1997, vol. 25, No. 12, pp. 2541-2542.

Rohrwild et al., *Inosine containing primers for mRNA differential display*, Trends in Genetics, 1995, vol. 11, No. 8, p. 300.

Internatiional Search Report from PCT application No. PCT/IS02/34056.

Li, N., Anal Bioanal Chem, 374:269-273 (2002).

Meldrum, D. et al., Genome Research, 10:1081-1092 (2000).

Wiesner, R.J. et al., Nucleic Acids Research, 20:5863-5864 (1992).

Wiesner, R.J. et al., Biochemical and Biophysical Research Communications, 183:553-59 (1992).

(Continued)

*Primary Examiner*—Suryaprabha Chunduru
(74) *Attorney, Agent, or Firm*—Mark J. FitzGerald

(57) ABSTRACT

The invention provides compositions, methods and systems for dynamic transcription profiling of two or more samples. The method of the invention comprises the uses of sample-specific primers for cDNA synthesis and for subsequent amplification of the synthesized cDNAs. The levels of abundance of genes are compared between samples for the identification of differentially expressed genes.

20 Claims, 7 Drawing Sheets

OTHER PUBLICATIONS

Abbs, S. et al., J Med Genet, 28:304-311 (1991). "A convenient multiplex PCR system for the detection of dystrophin gene deletions: a comparative analysis with cDNA hybridisation shows mistypings by both methods."

Van Eekelen, J.A.M. et al., Clinical Biochemistry, 33(6):457-464 (2000). "Quantitative analysis of cytokeratin 20 gene expression using RT-PCR and capillary electrophoresis with fluorescent DNA detection."

* cited by examiner

DNAs

Primer 2:

A) (unique sequence C)$_{10-16}$(Z)$_{2-4}$(XXXXX)$_{5-10}$

X= A, T, G, C

Z= artificial base, pairing with all four nucleotides

B) (unique sequence C)$_{15-30}$(XXXXX)$_{5-10}$

Primer 2 a)

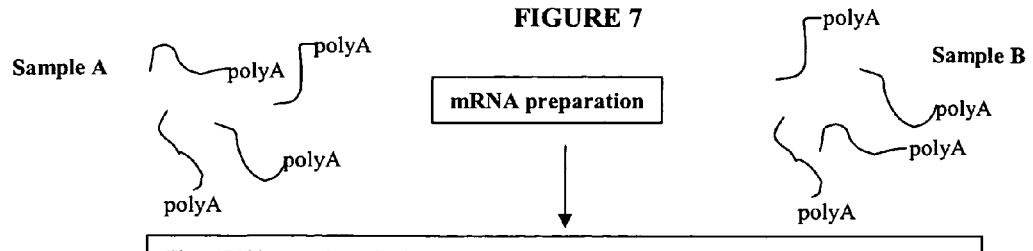

First cDNA strand synthesis using a first primer (1A or 1B) comprising a sample-specific-sequence tag (Tag A or Tag B):     (Tag A or Tag B)$_{20-24}$ (dT)$_{12-16}$ VN
Preferably Tag A or B would be GC rich at 5' and AT rich at 3'(e.g., >70% GCs or ATs);
Also preferably Tag A or B would comprise artificial nucleotides.

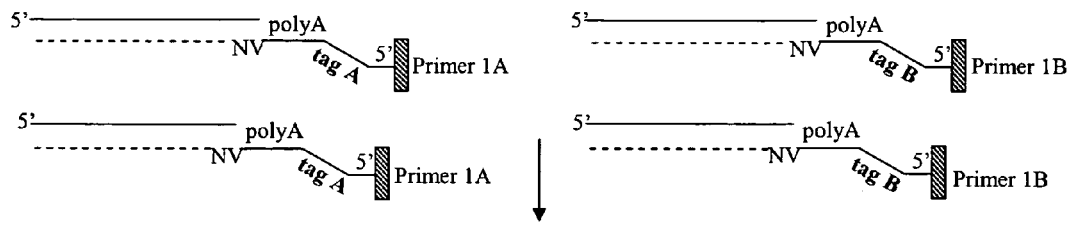

Second cDNA strand synthesis using a common second primer (2) comprising a first arbitrary sequence tag X and a second arbitrary sequence tag Y. There may be one or more degenerate bases (Z) between tag X and tag Y. Tag Y allows the generation of second strand cDNAs for a specific set of genes:

$$(\text{TagX})_{10-12} (Z)_4 (\text{TagY})_{6-7}.$$

Preferably Tag X would be GC rich at 5' and AT rich at 3'(e.g., >70% GCs or ATs); Also preferably Tag X would comprise artificial nucleotides.

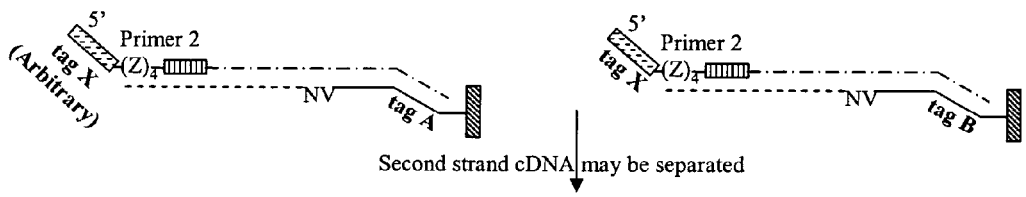

Second strand cDNA may be separated

PCR amplification using primers 3 and 4:
  - Primer 4 comprises the sequence of TagX and is common for both samples;
  - Primer 3 comprises the sequence of either tag A or Tag B (sample-specific); and
  - Primer 3 is differentially labeled (e.g., by fluorescent labels).

The amplified PCR products would be differentially labeled according to their source.

The abundance of an amplified PCR product is resolved by capillary electrophoresis after each amplification cycle.

The abundance of the amplified PCR product is compared between the two samples.

METHODS AND SYSTEMS FOR DYNAMIC GENE EXPRESSION PROFILING

RELATED APPLICATIONS

This application is a Divisional of U.S. Ser. No. 10/113,034, filed Apr. 1, 2002, which claims priority to U.S. provisional application 60/346,140, filed Oct. 24, 2001, the entirety of each of which is hereby incorporated by reference.

FIELD OF THE INVENTION

The invention is related to transcriptional profiling technology.

BACKGROUND

The introduction of genomics has been instrumental in accelerating the pace of drug discovery. The genomic technologies have proved their value in finding novel drug targets. Further improvement in this area will provide more efficient tools resulting in faster and more cost efficient development of potential drugs.

The drug discovery process includes several steps: the identification of a potential biochemical target associated with disease, screening for active compounds and further chemical design, preclinical tests, and finally clinical trials. The efficiency of this process is still far from perfect: it is estimated that about 75% of money spent in the R&D process went to fund failed projects. Moreover, the later in the product development a failure occurs, the bigger are losses associated with this project. Therefore, there is a need for early elimination of future failures to considerably cut costs of the whole drug development process. Thus, the quality of the original molecular target becomes a decisive factor for cost-effective drug development.

One approach that promises to impact on the process of target identification and validation is transcription profiling. This method compares expression of genes in a specific situation: for example, between disease and normal cells, between control and drug-treated cells or between cells responding to treatment and those resistant to it. The information generated by this approach may directly identify specific genes to be targeted by a therapy, and, importantly, reveals biochemical pathways involved in disease and treatment. In brief, it not only provides biochemical targets, but at the same time, a way to assess the quality of these targets. Moreover, in combination with cell-based screening, transcription profiling is positioned to dramatically change the field of drug discovery. Historically, screening for a potential drug was successfully performed using phenotypic change as a marker in functional cellular system. For example, growth of tumor cells in culture was monitored to identify anticancer drugs. Similarly, bacterial viability was used in assays aimed at identifying antibiotic compounds. Such screens were typically conducted without prior knowledge of the targeted biochemical pathway. In fact, the identified effective compounds revealed such pathways and pointed out the true molecular target, enabling subsequent rational design of the next generations of drugs.

Modern tools of transcription profiling can be used to design novel screening methods that will utilize gene expression in place of phenotypic changes to assess effectiveness of a drug. For example, these methods are described in U.S. Pat. Nos. 5,262,311; 5,665,547; 5,599,672; 5,580,726; 6,045,988 and 5,994,076, as well as Luehrsen et al. (1997, Biotechniques, 22:168-74; Liang and Pardee (1998, Mol Biotechnol. 10:261-7). Such approach will be invaluable for drug discovery in the field of central nervous system (CNS) disorders such as dementia, mild cognitive impairment, depression, etc., where phenotypic screening is inapplicable, but desired transcription profile can be readily established and linked to particular disorders. Once again, the identified effective compounds will reveal the underlying molecular processes. In addition, this method can be instrumental for development of improved versions of existent drugs, which act at several biochemical targets at the same time to generate the desired pharmacological effect. In such case the change in the transcriptional response may be a better marker for drug action than selection based on optimization of binding to multiple targets.

Prior to the instant invention, the most advanced method of transcription profiling is based on technology using DNA microarrays, for example, as reviewed in Greenberg, 2001 Neurology 57:755-61; Wu, 2001, J Pathol. 195:53-65; Dhiman et al., 2001, Vaccine 20:22-30; Bier et al., 2001 Fresenius J Anal Chem. 371:151-6; Mills et al., 2001, Nat Cell Biol. 3:E175-8; and as described in U.S. Pat. Nos. 5,593,839; 5,837,832; 5,856,101; 6,203,989; 6,271,957; and 6,287,778. DNA microarray is a method which performs simultaneous comparison of the expression of several thousand genes in a given sample by assessing hybridization of the labeled polynucleotide samples, obtained by reverse transcription of mRNAs, to the DNA molecules attached to the surface of the test array. While the technology provides valuable information about transcriptional changes, it is far from perfect.

First of all, this technology is limited to the pool of genes presented in the microarray. The current printing methods allows placement of 10,000-15,000 genes on a single chip, which is essentially a number of genes expressed in a particular cell type. Given the diversity of cell types, it requires development of specific arrays for specific cell types. While theoretically possible, this task is hard to acheive, since it requires knowledge about gene pool expressed in these cells prior to microarray manufacturing.

Moreover, the number of transcripts in a tissue sample is even higher than in a cellular sample and exceeds the current capacity of the microarray. In addition, some changes in gene expression result from alternative splicing, which further increases the number of transcripts that need to be assessed. The only possibility to overcome these difficulties will be to develop multiple arrays that will cover the entire genome, including alternatively spliced genes. This approach will significantly increase the cost of a single experiment and will require a large biological sample, perhaps larger than is reasonably available.

Secondly, at present, DNA microarrays do not provide quantitatively accurate data, and observed changes in gene expression have to be confirmed by an independent methods, for example, quantitative PCR (Q-PCR).

In addition, a typical microarray experiment includes several manual steps which affect the reproducibility of this method.

And finally, the expression of rare transcripts, which may be of particular interest, can not be accurately measured by microarrays using current detection techniques. These limitations demonstrate a need to develop alternative methods to perform transcription profiling, preferably one that 1) will not require prior knowledge of the sequences of the expressed gene pool before the assay but by itself will provide this information during/after the assay; 2) will measure quantitative changes in the level of expressed transcripts; 3) will be able to detect expression of rare genes; and 4) can be automated.

Capillary electrophoresis has been used to quantitatively detect gene expression. Rajevic at el. (2001, Pflugers Arch. 442(6 Suppl 1):R190-2) discloses a method for detecting differential expression of oncogenes by using seven pairs of primers for detecting the differences in expression of a number of oncogenes simultaneously. Sense primers were 5' end-labelled with a fluorescent dye. Multiplex fluorescent RT-PCR results were analyzed by capillary electrophoresis on ABI-PRISM 310 Genetic Analyzer. Borson et al. (1998, Biotechniques 25:130-7) describes a strategy for dependable quantitation of low-abundance mRNA transcripts based on quantitative competitive reverse transcription PCR (QC-RT-PCR) coupled to capillary electrophoresis (CE) for rapid separation and detection of products. George et al., (1997, J Chromatogr B Biomed Sci Appl 695:93-102) describes the application of a capillary electrophoresis system (ABI 310) to the identification of fluorescent differential display generated EST patterns. Odin et al. (1999, J Chromatogr B Biomed Sci Appl 734:47-53) describes an automated capillary gel electrophoresis with multicolor detection for separation and quantification of PCR-amplified cDNA.

Omori et al. (2000, Genomics 67:140-5) measures and compares the amount of commercially purchased α-globin mRNA by competitive PCR in two independently reverse transcribed cDNA samples using oligo(dT) or oligo(dU) primers. The oligo(dT) or oligo(dU) primers share a 3' oligo(dT) or oligo(dU) sequence and a 5' common sequence. In addition the oligo(dT) or oligo(dU) primer for each sample also contains a unique 29 nucleotide sequence between the 3' oligo(dT) or oligo(dU) sequence and the 5' common sequence. After the synthesis of first strand cDNA, PCR is performed to amplify the cDNA using a gene-specific primer and a primer complementary to the common sequence which is labeled with a unique label. The amplified PCR products are then analyzed by spotting onto a detection plate of a fluorescence scanner.

There is a need in the art for simple, sensitive method for simultaneous quantitative detection of gene expression profile in multiple samples.

SUMMARY OF THE INVENTION

The invention provides methods and compositions for expression profiling of two or more samples.

The invention provides a method for comparing gene expression profiles of two or more samples, the method comprising:
  (a) synthesizing a plurality of first strand cDNAs from a first sample using a first oligonucleotide primer comprising a sample-specific sequence tag, where the sample-specific sequence tag is GC rich at its 5' terminal and At rich at its 3' terminal;
  (b) selectively amplifying at least a subset of the cDNA so as to generate one or more sample-specific amplified products;
  (c) detecting the abundance of one or more the sample-specific amplified products, where the abundance determines an expression profile of one or more genes in the first sample; and
  (d) comparing the expression profile of the one or more genes in the first sample with an expression profile of the one or more genes in a second sample, where a difference in the expression profile indicates differential expression of the one or more genes in the two samples.

The invention also provides a method for comparing gene expression profiles of two or more samples, the method comprising:
  (a) synthesizing a plurality of first strand cDNAs from a first sample using a first oligonucleotide primer comprising a sample-specific sequence tag, where the first oligonucleotide primer comprises at least one degenerate nucleotide;
  (b) selectively amplifying at least a subset of the cDNA so as to generate one or more sample-specific amplified products;
  (c) detecting the abundance of one or more the sample-specific amplified products, where the abundance determines an expression profile of one or more genes in the first sample; and
  (d) comparing the expression profile of the one or more genes in the first sample with an expression profile of the one or more genes in a second sample, where a difference in the expression profile indicates differential expression of the one or more genes in the two samples.

The invention provides a method for comparing gene expression profiles of two or more samples, the method comprising:
  (a) synthesizing a plurality of first strand cDNAs from a first sample using a first oligonucleotide primer comprising a sample-specific sequence tag, where the sample-specific sequence tag comprises at least one artificial nucleotide which shows a preference of base pairing with another artificial nucleotide over a conventional nucleotide;
  (b) selectively amplifying at least a subset of the cDNA so as to generate one or more sample-specific amplified products;
  (c) detecting the abundance of one or more the sample-specific amplified products, where the abundance determines an expression profile of one or more genes in the first sample; and
  (d) comparing the expression profile of the one or more genes in the first sample with an expression profile of the one or more genes in a second sample, where a difference in the expression profile indicates differential expression of the one or more genes in the two samples.

The invention further provides a method for comparing gene expression profiles of two or more samples, the method comprising:
  (a) synthesizing a plurality of first strand cDNAs from a first sample using a first oligonucleotide primer comprising a sample-specific sequence tag, where the sample-specific sequence tag is GC rich at its 5' terminal and At rich at its 3' terminal;
  (b) selectively synthesizing one or more second strand cDNAs complementary to the first strand cDNAs using a second oligonucleotide primer comprising a first arbitrary sequence tag;
  (c) amplifying the one or more second strand cDNA so as to generate one or more sample-specific amplified products;
  (d) detecting the abundance of one or more the sample-specific amplified products, where the abundance determines an expression profile of one or more genes in the first sample; and
  (e) comparing the expression profile of the one or more genes in the first sample with an expression profile of the one or more genes in a second sample, where a difference in the expression profile indicates differential expression of the one or more genes in the two samples.

The invention still provides a method for comparing gene expression profiles of two or more samples, the method comprising:

(a) synthesizing a plurality of first strand cDNAs from a first sample using a first oligonucleotide primer comprising a sample-specific sequence tag, where the first oligonucleotide primer comprises at least one degenerate nucleotide;
(b) selectively synthesizing one or more second strand cDNAs complementary to the first strand cDNAs using a second oligonucleotide primer comprising a first arbitrary sequence tag;
(c) amplifying the one or more second strand cDNA so as to generate one or more sample-specific amplified products;
(d) detecting the abundance of one or more the sample-specific amplified products, where the abundance determines an expression profile of one or more genes in the first sample; and
(e) comparing the expression profile of the one or more genes in the first sample with an expression profile of the one or more genes in a second sample, where a difference in the expression profile indicates differential expression of the one or more genes in the two samples.

The invention further provides a method for comparing gene expression profiles of two or more samples, the method comprising:
(a) synthesizing a plurality of first strand cDNAs from a first sample using a first oligonucleotide primer comprising a sample-specific sequence tag, where the sample-specific sequence tag comprises at least one artificial nucleotide which shows a preference of base pairing with another artificial nucleotide over a conventional nucleotide;
(b) selectively synthesizing one or more second strand cDNAs complementary to the first strand cDNAs using a second oligonucleotide primer comprising a first arbitrary sequence tag;
(c) amplifying the one or more second strand cDNA so as to generate one or more sample-specific amplified products;
(d) detecting the abundance of one or more the sample-specific amplified products, where the abundance determines an expression profile of one or more genes in the first sample; and
(e) comparing the expression profile of the one or more genes in the first sample with an expression profile of the one or more genes in a second sample, where a difference in the expression profile indicates differential expression of the one or more genes in the two samples.

The invention provides a method of identifying a modulator which regulates one or more gene expression in a sample, the method comprising:
(a) synthesizing a plurality of first strand cDNAs, before contacting the sample with the modulator, using a first oligonucleotide primer comprising a sample-specific sequence tag, where the sample-specific sequence tag is GC rich at its 5' terminal and At rich at its 3' terminal;
(b) selectively amplifying at least a subset of the cDNA so as to generate one or more sample-specific amplified products;
(c) detecting the abundance of one or more the sample-specific amplified products, where the abundance determines an expression profile of one or more genes in the sample; and
(d) comparing the expression profile of the one or more genes in the sample before contacting with the modulator with an expression profile of the one or more genes in the sample after contacting the modulator, where a difference in the expression profile indicates the modulator regulating one or more gene expression in the sample.

The invention also provides a method of identifying a modulator which regulates one or more gene expression in a sample, the method comprising:
(a) synthesizing a plurality of first strand cDNAs, before contacting the sample with the modulator, using a first oligonucleotide primer comprising a sample-specific sequence tag, where the first oligonucleotide primer comprises at least one degenerate nucleotide;
(b) selectively amplifying at least a subset of the cDNA so as to generate one or more sample-specific amplified products;
(c) detecting the abundance of one or more the sample-specific amplified products, where the abundance determines an expression profile of one or more genes in the sample; and
(d) comparing the expression profile of the one or more genes in the sample before contacting with the modulator with an expression profile of the one or more genes in the sample after contacting the modulator, where a difference in the expression profile indicates the modulator regulating one or more gene expression in the sample.

The invention further provides a method of identifying a modulator which regulates one or more gene expression in a sample, the method comprising:
(a) synthesizing a plurality of first strand cDNAs, before contacting the sample with the modulator, using a first oligonucleotide primer comprising a sample-specific sequence tag, where the sample-specific sequence tag is GC rich at its 5' terminal and At rich at its 3' terminal;
(b) synthesizing one or more second strand cDNAs using a second oligonucleotide primer comprising a first arbitrary sequence tag;
(c) amplifying the second strand cDNAs so as to generate one or more sample-specific amplified products;
(d) detecting the abundance of one or more the sample-specific amplified products, where the abundance determines an expression profile of one or more genes in the sample; and
(e) comparing the expression profile of the one or more genes in the sample before contacting with the modulator with an expression profile of the one or more genes in the sample after contacting the modulator, where a difference in the expression profile indicates the modulator regulating one or more gene expression in the sample.

The invention still provides a method of identifying a modulator which regulates one or more gene expression in a sample, the method comprising:
(a) synthesizing a plurality of first strand cDNAs, before contacting the sample with the modulator, using a first oligonucleotide primer comprising a sample-specific sequence tag, where the first oligonucleotide primer comprises at least one degenerate nucleotide;
(b) synthesizing one or more second strand cDNAs using a second oligonucleotide primer comprising a first arbitrary sequence tag;
(c) amplifying the second strand cDNAs so as to generate one or more sample-specific amplified products;
(d) detecting the abundance of one or more the sample-specific amplified products, where the abundance determines an expression profile of one or more genes in the sample; and
(e) comparing the expression profile of the one or more genes in the sample before contacting with the modulator with an expression profile of the one or more genes in the sample after contacting the modulator, where a difference in the expression profile indicates the modulator regulating one or more gene expression in the sample.

In a preferred embodiment, the step (a) of the subject method comprises reverse transcribing RNA from two or more sample sources into first strand cDNA, and where the cDNA is differentially tagged according to their sources.

Preferably, the plurality of first strand cDNAs is synthesized by reverse transcription using total RNAs or mRNAs derived from the first sample.

Preferably, the second sequence in the second oligonucleotide primer is gene-family-specific.

More preferably, the second sequence in the second oligonucleotide primer is a sequence encoding a peptide specific for a protein family.

Still more preferably, the second sequence comprises a sequence encoding a signature sequence motif for a specific protein family.

Preferably, the protein family is selected from the group consisting of: receptor tyrosine kinases, G protein coupled receptors, seven transmembrane receptors, ion channels, cytokine receptors, tumor markers, MAPK cascade kinases, transcriptional factors, GTPases, ATPases, and development protein markers.

Preferably, a third oligonucleotide primer comprises the sequence-specific sequence tag of the first oligonucleotide primer is used for the amplifying so as to generate one or more sample-specific amplified products.

Also preferably, at least one of the two or more samples is derived form the group consisting of: a normal sample, a disease sample, a sample at a given development stage or condition, a sample prior to a given treatment stage or condition, a sample after a given treatment stage or condition, and a sample at a given culturing stage or condition.

Still preferably, at least one of the two or more samples is derived from the group consisting of: an animal, an organ, a tissue type, and a cell type.

In one embodiment, at least one sample is derived from a normal individual and at least another sample is derived from a disease individual.

In another embodiment, at least one sample is derived from a development stage of an individual and at least another sample is derived from a different development stage of the same individual.

In yet another embodiment, at least one sample is derived from a disease stage of an individual and at least another sample is derived from a different disease stage of the same individual.

In still another embodiment, at least one sample is derived from a stage of a disease treatment of an individual and at least another sample is derived from a different stage of the same disease treatment of the same individual.

In another embodiment, at least one sample is derived from an individual who was exposed to an environmental factor and at least another sample is derived from an individual who was not exposed to the same environmental factor or who was exposed to the environmental factor at a different concentration.

In one embodiment, the one or more second strand cDNAs are amplified by PCR so as to generate one or more amplified PCR products.

Preferably, the one or more amplified products are sampled at a predetermined time or cycle interval during the amplification.

In one embodiment, the one or more amplified products are sampled after each cycle of the amplification.

In another embodiment, the one or more amplified products are sampled after one or more predetermined cycles, for example, after cycle 2, 5, 10, 25, 30, or cycle 45.

In one embodiment, the one or more amplified products are sampled by withdrawing 1% to 40% (v/v) of the reaction mixture, preferably, by withdrawing 1% to 30% (v/v) of the reaction mixture.

In another embodiment, the reaction mixture is replenished after each sampling with equivalent volume of a mixture comprising dNTPs, primers, necessary reagents, and a DNA polymerase at the same concentration as the starting reaction mixture.

Preferably, the abundance is detected for each sampled amplified product.

Preferably, the subject method further comprises separating the one or more amplified products before detecting the abundance of the one or more amplified products.

In one embodiment, the one or more amplified products are separated and their abundance detected by chromatography.

In another embodiment, the one or more amplified products are separated and their abundance detected by mass spectrometry.

In yet another embodiment, the one or more amplified products are separated and their abundance detected by electrophoresis.

Preferably, the one or more amplified products are separated and their abundance detected by capillary electrophoresis.

In one embodiment, the sample-specific sequence in the first oligonucleotide primer is 15-30 nucleotides in length, more preferably, 20-24 nucleotides in length.

In a preferred embodiment, the first oligonucleotide primer further comprises a sequence of 5' oligo(dT)$_n$VN 3', where n is at least 5; V is dATP, dGTP, or dCTP; and N is dTTP (or dUTP), dATP, dGTP, or dCTP.

Preferably, n is 12-16 in 5' oligo(dT)$_n$VN 3'.

Also preferably, in the first oligonucleotide primer, the sample-specific sequence tag is located at the 5' of oligo(dT)$_n$VN.

Preferably, the second oligonucleotide primer of the subject method further comprises a second sequence which is complementary to a subset of the first strand cDNAs so as to permit the synthesis of one or more second strand cDNAs.

More preferably, in the second oligonucleotide primer, the second sequence is located 3' of the first arbitrary sequence.

Also more preferably, the second oligonucleotide further comprises a sequence of $(Z)_m$ between the first and second sequences, where Z is a nucleotide which can form base pair with any of A, T, G, or C, and m is at least 2. Preferably, m is 4.

In one embodiment, the second sequence in the second oligonucleotide primer is 5-10 nucleotides in length.

In another embodiment, the second sequence in the second oligonucleotide primer is 6-7 nucleotides in length.

Preferably, the second sequence in the second oligonucleotide primer is a palindromic sequence.

In one embodiment, the first arbitrary sequence in the second oligonucleotide primer is 15-30 nucleotides in length, preferably 20 nucleotides in length.

In another embodiment, the first arbitrary sequence in the second oligonucleotide primer comprises an A-T rich region and a G-C rich region.

Preferably, the G-C rich region is located at 5' of the A-T rich region.

Preferably, the second oligonucleotide primer used is the same for the two or more samples to be compared.

In a preferred embodiment, the amplifying step of the subject method further comprises using a fourth oligonucleotide primer which comprises the first arbitrary sequence tag of the second oligonucleotide primer.

Preferably, the fourth oligonucleotide primer used is the same for the two or more samples to be compared.

In one embodiment, the first strand cDNA is synthesized in a solution without attaching to a solid support.

In another embodiment, the first strand cDNA is synthesized attaching to a solid support.

Preferably, the solid support is a microparticle or an inner wall of a reaction tube.

In a preferred embodiment, the subject method of the invention further comprises separating the one or more second strand cDNA from the plurality of first strand cDNA before amplifying the one or more second strand cDNAs.

In one embodiment, the third oligonucleotide primer used in the subject method is linked to a detectable label.

Preferably, the detectable is selected from a group consisting of: fluorescent labels, radioactive labels, colorimetrical labels, magnetic labels, and enzymatic labels.

More preferably, the detectable label is a fluorescent label.

In a preferred embodiment, the third oligonucleotide primer used for each of the two or more samples is labeled with a sample-specific label.

In one embodiment according to the subject method of the invention, the difference in the expression profile of the one or more genes is measured by a ratio of sample-specific detectable labels on amplified products from the genes between two or more samples.

Preferably, the method further comprises generating an amplification plot (signal intensity as a function of amplification cycle number), calculating a threshold cycle number (Ct) of amplification for each of the one or more genes based on the signal intensity of each PCR fragment. Operational differential expression of particular gene is determined as a difference in threshold cycle number (Ct) for this gene in two (or more) samples more than one cycle in value. The threshold cycle number is further used to derive copy number for each gene and to measure the difference in the expression by a ratio of copy numbers for gene in two or more samples.

The method also comprises generating an plot of the rate of signal intensity change as a function of number of amplification cycles [derivative of Signal Intensity as a function of cycle numer, d(Signal Intensity)/d(cycle number)] for each amplified gene. The alternative threshold cycle (aCt), determined as a cycle number corresponding to the maximal value of d(Signal Intensity)/d(cycle number) for each amplified gene from one sample, is compared to the aCt for the same gene from another sample. Difference in one cycle between aCt values for the same gene in two or more samples is defined as alternative operational differential expression.

Also preferably, the method further comprises collecting PCR fragment or PCR fragments corresponding to one or more genes which display operational differential expression or alternative operational differential expression, and identifying the sequence of the one or more genes.

In one embodiment, the sequence identities of the one or more genes which are differentially expressed are identified by DNA sequencing.

In one embodiment, the subject method may further comprise a second amplification reaction using the one or more amplified products from the first amplification to generate one or more secondly amplified products and detecting the abundance of the one or more secondly amplified products.

Preferably, the amplifying step of the subject method is performed by PCR.

The subject method of the invention may further comprise a nested PCR reaction as a second amplification reaction.

The present invention provides a composition for detecting the level of gene expression, comprising a first oligonucleotide primer, where the first oligonucleotide primer comprises a sample-specific sequence tag and where the first oligonucleotide primer comprises at least one degenerate nucleotide.

In one embodiment, the first oligonucleotide primer is provided as a mixture of primers comprising [5'-(specific sequence tag)$_{20-24}$T$_{12-16}$AN-3',5'-(specific sequence tag)$_{20-24}$T$_{12-16}$CN-3', and 5'-(specific sequence tag)$_{20-24}$T$_{12-16}$GN-3'].

The present invention also provides a composition for detecting the level of gene expression, comprising a first oligonucleotide primer, where the first oligonucleotide primer comprises a sample-specific sequence tag and where the sample-specific sequence tag is GC rich at its 5' terminal and AT rich at its 3' terminal.

Preferably, the subject composition further comprises a second oligonucleotide primer.

More preferably, the second oligonucleotide primer comprises a first arbitrary sequence tag.

Preferably, the second primer further comprises a second sequence which is complementary to a sequence of the first strand cDNA.

The subject composition may further comprise a third oligonucleotide primer comprising the sequence-specific sequence tag of the first oligonucleotide primer.

The subject composition may further comprise a fourth oligonucleotide primer which comprises the first arbitrary sequence tag.

The subject composition may further comprise one or more components selected from the group of: a reverse transcriptase, a DNA polymerase, a reaction buffer for the reverse transcriptase, a reaction buffer for the DNA polymerase, and dNTPs.

The invention provides a kit for detecting the level of gene expression, comprising a first oligonucleotide primer, wherein the first oligonucleotide primer comprises a sample-specific sequence tag and wherein the first oligonucleotide primer comprises at least one degenerate nucleotide, and packaging material thereof.

The invention also provides a kit for detecting the level of gene expression, comprising a first oligonucleotide primer, wherein the first oligonucleotide primer comprises a sample-specific sequence tag and wherein the sample-specific sequence tag is GC rich at its 5' terminal and AT rich at its 3' terminal, and packaging material thereof.

The kit of the present invention may also comprise a second oligonucleotide primer.

Preferably, the second oligonucleotide primer comprises a first arbitrary sequence tag.

The kit of the present invention may further comprise a third oligonucleotide primer comprising the sequence-specific sequence tag of the first oligonucleotide primer.

The kit of the present invention may still further comprise a fourth oligonucleotide primer which comprises the first arbitrary sequence tag.

Preferably, the second primer further comprises a second sequence which is complementary to a sequence of the first strand cDNA.

Also preferably, the kit of the present invention further comprises one or more components selected from the group of: a reverse transcriptase, a DNA polymerase, a reaction buffer for said reverse transcriptase, a reaction buffer for said DNA polymerase, and dNTPs.

BRIEF DESCRIPTION OF DRAWINGS

FIG. 7 is a diagram showing the method of transcriptional profiling according to a preferred embodiment of the invention.

DETAILED DESCRIPTION OF THE INVENTION

Figure 1:
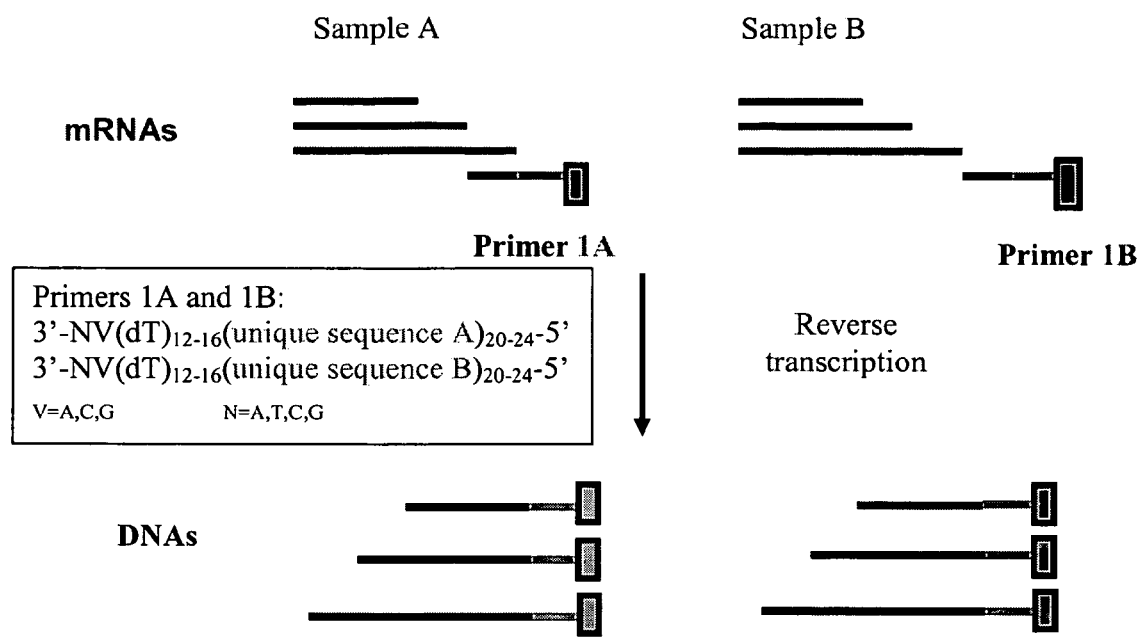
FIG. 1 is a diagram showing the reverse transcription of mRNAs from two samples using oligo-dT primers with sample-specific sequence tags according to one embodiment of the invention. The resulting cDNAs from each sample are labeled by sample-specific tags.
Figure 2:
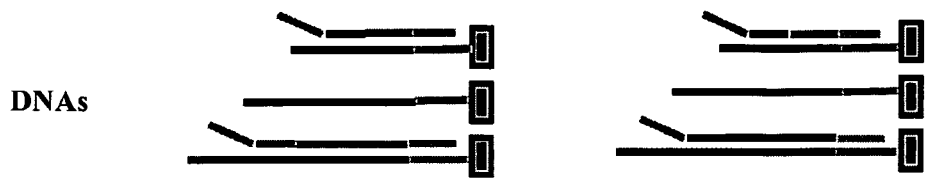
FIG. 2 is a diagram showing the second strand cDNA synthesis of selected genes using a primer comprising a gene-family-specific sequence according to one embodiment of the invention.
Figure 2:

Definitions:

As used herein, the term "sample" refers to a biological material which is isolated from its natural environment and containing a polynucleotide. A "sample" according to the invention may consist of purified or isolated polynucleotide, or it may comprise a biological sample such as a tissue sample, a biological fluid sample, or a cell sample comprising a polynucleotide. A biological fluid includes blood, plasma, sputum, urine, cerebrospinal fluid, lavages, and leukophoresis samples. A sample of the present invention may be any plant, animal, bacterial or viral material containing a polynucleotide.

As defined herein, a "tissue" is an aggregate of cells that perform a particular function in an organism. The term "tissue" as used herein refers to cellular material from a particular physiological region. The cells in a particular tissue may comprise several different cell types. A non-limiting example of this would be brain tissue that further comprises neurons and glial cells, as well as capillary endothelial cells and blood cells. The term "tissue" also is intended to encompass a plurality of cells contained in a sublocation on the tissue microarray that may normally exist as independent or non-adherent cells in the organism, for example immune cells, or blood cells. The term is further intended to encompass cell lines and other sources of cellular material that now exist which represent specific tissue types (e.g., by virtue of expression of biomolecules characteristic of specific tissue types).

As used herein, "plurality" refers to more than two. Plurality, according to the invention, can be 3 or more, 100 or more, or 1000 or more, for example, up to the number of cDNAs corresponding to all mRNAs in a sample.

As used herein "different types of tissues" refers to tissues which are preferably from different organs or which are at least from anatomically and histologically distinct sites in the same organ.

As used herein "a cell sample" is distinguished from a tissue sample in that it comprises a cell or cells which are disassociated from other cells.

As defined herein, "an individual" is a single organism and includes humans, animals, plants, multicellular and unicellular organisms.

As used herein, a "sample-specific sequence" refers to a polynucleotide sequence which is used to identify a polynucleotide molecule derived from a specific sample source. A "sample-specific sequence" of the present invention indicates the sample source of an isolated or synthesized polynucleotide and distinguishes an isolated or synthesized polynucleotide of one sample from that of another sample. Therefore, a sample-specific sequence has a unique characteristic which can be identified. The unique characteristic of a sample-specific sequence may be a specific sequence identity or a specific sequence length. If a specific sequence identity is used, one sample-specific sequence should be different from another sample-specific sequence in at least one nucleotide, for example, in at least 2, or 3, or 4, or 5, or 10, or 15, or 20, or more, up to 60 nucleotides. If a specific sequence length is used, one sample-specific sequence should be different in length from another sample-specific sequence in at least one nucleotide, for example, in at least 2, or 3, or 4, or 5, or 10, or 15, or 20, or more, up to 50 nucleotides.

As used herein, a "polynucleotide molecule derived from a specific sample" may be a polynucleotide isolated from the specific sample, or it may be a polynucleotide synthesized from the specific sample, e.g., through the technologies of reverse transcription or polymerase chain reaction (PCR), ligase chain reaction (LCR), and polynucleotide-specific based amplification (NSBA), strand displacement amplification (SDA) and any other technologies known in the art.

As used herein, the term "different samples" refers to two or more samples which are ti be compared according to the subject methods of the invention, whether or not they contain identical tissue or samples from different sources. Different sources can be, but are not limited to, a disease source and a normal source; different cell types, different tissue or organ types; different individuals; samples subjected to different environmental exposures; different development stages; different stages of a disease; and different stages of treatment.

As used herein, the term "amplified product" refers to polynucleotides which are copies of a portion of a particular polynucleotide sequence and/or its complementary sequence, which correspond in nucleotide sequence to the template polynucleotide sequence and its complementary sequence. An "amplified product," according to the invention, may be DNA or RNA, and it may be double-stranded or single-stranded.

As used herein, the terms "synthesis" and "amplification" are used interchangeably to refer to a reaction for generating a copy of a particular polynucleotide sequence or increasing in copy number or amount of a particular polynucleotide sequence. It may be accomplished, without limitation, by the in vitro methods of polymerase chain reaction (PCR), ligase chain reaction (LCR), polynucleotide-specific based amplification (NSBA), or any other method known in the art. For example, polynucleotide amplification may be a process using a polymerase and a pair of oligonucleotide primers for producing any particular polynucleotide sequence, i.e., the target polynucleotide sequence or target polynucleotide, in an amount which is greater than that initially present.

As used herein, the term "selectively," when referred to the amplification or synthesis of polynucleotide, refers to amplifying or synthesizing a selected group of polynucleotides comprising a complementary sequence. The selection is achieved by using a specific oligonucleotide primer in an amplification or synthesis reaction. For example, a group of second strand cDNAs may be selectively synthesized by using a second oligonucleotide comprising a sequence (e.g., the second sequence as described herein after) which is complementary to a gene family specific sequence.

As used herein, the term "at least a subset" refers to the amplification or synthesis of either all polynucleotides in a reaction or less than all polynucleotide templates in an amplification or synthesis reaction. For example, a subset of polynucleotides (e.g., first strand cDNAs) may be amplified or synthesized by the use of a specific oligonucleotide primer which selectively amplifies or synthesizes a group (e.g., a gene family) of polynucleotides from the population of all first strand cDNAs.

As used herein, a "target polynucleotide" is a polynucleotide sequence whose level of expression is to be analyzed. A target polynucleotide may be isolated or amplified before its expression level is analyzed. For example, a target polynucleotide may be a sequence that lies between the hybridization regions of two members of a pair of oligonucleotide primers which are used to amplify it. A target polynucleotide may be RNA or DNA, for example, it may be mRNA or cDNA, a coding region of a gene or a portion thereof. A target polynucleotide sequence generally exists as part of a larger "template" sequence; however, in some cases, a target sequence and the template are the same. Although "template sequence" generally refers to the polynucleotide sequence initially present, the products from an amplification reaction may also be used as template sequence in subsequent amplification reactions. A "target polynucleotide" or a "template sequence" may be a normal (e.g., wild type) or a mutant polynucleotide that is or includes a particular sequence.

As used herein, the term "RT-PCR" refers to coupled reverse transcription and polymerase chain reaction. This method of amplification uses an initial step in which a specific oligonucleotide, oligo dT, or a mixture of random primers is used to prime reverse transcription of RNA into a first single-stranded cDNA; this cDNA is then amplified using standard amplification techniques, e.g. PCR, so as to generate a second complementary strand and double-stranded cDNA.

As used herein, an "oligonucleotide primer" refers to a polynucleotide molecule (i.e., DNA or RNA) capable of annealing to a polynucleotide template and providing a 3' end to produce an extension product which is complementary to the polynucleotide template. The conditions for initiation and extension usually include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.) and at a suitable temperature. The primer according to the invention may be single- or double-stranded. The primer is single-stranded for maximum efficiency in amplification, and the primer and its complement form a double-stranded polynucleotide. But it may be double-stranded. "Primers" useful in the present invention are less than or equal to 100 nucleotides in length, e.g., less than or equal to 90, or 80, or 70, or 60, or 50, or 40, or 30, or 20, or 15, or equal to 10 nucleotides in length.

As used herein, the term "arbitrary sequence" is defined as being based upon or subject to individual judgement or discretion. In some instances, the arbitrary sequence can be entirely random or partly random for one or more bases. In other instances the arbitrary sequence can be selected to contain a specific ratio of each deoxynucleotide, for example approximately equal proportions of each deoxynucleotide or predominantly one deoxynucleotide, or to not contain a specific deoxynucleotide. The arbitrary sequence can be selected to contain, or not to contain, a recognition site for specific restriction endonuclease. The arbitrary sequence can be selected to either contain a sequence that is complementary to an mRNA or a cDNA of known sequence or to not contain sequence from an mRNA or cDNA of known sequence.

As used herein, "GC rich" refers to a continuous stretch of nucleotides (or 3' terminal nucleotide) which has a GC content of at least 60% GC (e.g., 3 bases of either G or C in a 5 base long stretch, 4 bases of either G or C in a 6 base long stretch, 5 bases of either G or C in a 7-8 base long stretch, 6 bases of either G or C in a 9-10 base long stretch, 7 bases of either G or C in a 11 base long stretch, 8 bases of either G or C in a 12-13 base long stretch, or 9 bases of either G or C in a 14-15 base long stretch, 10 bases of either G or C in a 16 base long stretch, 11 bases of either G or C in a 17-18 base long stretch, 12 bases of either G or C in a 19-20 base long stretch, 13 bases of either G or C in a 21 base long stretch, 14 bases of either G or C in a 22-23 base long stretch, 15 bases of either G or C in a 24 base long stretch, 16 bases of either G or C in a 25-26 base long stretch), or preferably at least 70% GC, or at least 80% GC or at least 90% GC or up to 100% GC.

As used herein, "AT rich" refers to a continuous stretch of nucleotides (i.e., including the 5' or 3' terminal nucleotide) which has a AT content of at least 60% AT (e.g., 3 bases of either A or T in a 5 base long stretch, 4 bases of either A or T in a 6 base long stretch, 5 bases of either A or T in a 7-8 base long stretch, 6 bases of either A or T in a 9-10 base long stretch, 7 bases of either A or T in a 11 base long stretch, 8 bases of either A or T in a 12-13 base long stretch, or 9 bases of either A or T in a 14-15 base long stretch, 10 bases of either A or T in a 16 base long stretch, 11 bases of either A or T in a 17-18 base long stretch, 12 bases of either A or T in a 19-20 base long stretch, 13 bases of either A or T in a 21 base long stretch, 14 bases of either A or T in a 22-23 base long stretch, 15 bases of either A or T in a 24 base long stretch, 16 bases of either A or T in a 25-26 base long stretch), or preferably at least 70% AT, or at least 80% AT or at least 90% AT or up to 100% AT.

As used herein, the term "gene family specific" sequence refers to a sequence of nucleotides on an oligonucleotide primer which anneals to more than one polynucleotide template in an amplification reaction. A "gene-family specific" primer is not required to be completely complementary to a template. Generally, a primer comprising a gene family specific sequence will anneal to at least 2, or 5, or at least 20, usually at least 50 and more, or usually at least 75 distinct genes as represented by distinct mRNAs or cDNAs in the sample. The term "distinct", when used to describe genes, refers any two genes are considered distinct if they comprise a stretch of at least 100 nts in their RNA coding regions in which the sequence similarity does not exceed 98%, as determined by FASTA (default settings). A "gene-family-specific sequence" is at least 4 nucleotides or more in length, e.g., at least 5, 6, 7, 8, 9, 10 or more and up to 50 nucleotides in length.

As used herein, "label" or "detectable label" refers to any atom or molecule which can be used to provide a detectable (preferably quantifiable) signal, and which can be operatively linked to a polynucleotide. Labels may provide signals detectable by fluorescence, radioactivity, colorimetry, gravimetry, X-ray diffraction or absorption, magnetism, enzymatic activity, mass spectrometry, binding affinity, hybridization radiofrequency, nanocrystals and the like. A primer of the present invention may be labeled so that the amplification reaction product may be "detected" by "detecting" the detectable label. "Qualitative or quantitative" detection refers to visual or automated assessments based upon the magnitude (strength) or number of signals generated by the label. A labeled polynucleotide (e.g., an oligonucleotide primer) according to the methods of the invention is labeled at the 5' end, the 3' end, or both ends, or internally. The label can be "direct", e.g., a dye, or "indirect", e.g., biotin, digoxin, alkaline phosphatase (AP), horse radish peroxidase (HRP). For detection of "indirect labels" it is necessary to add additional components such as labeled antibodies, or enzyme substrates to visualize the, captured, released, labeled polynucleotide fragment. In a preferred embodiment, an oligonucleotide primer is labeled with a fluorescent label. Suitable fluorescent labels include fluorochromes such as rhodamine and derivatives (such as Texas Red), fluorescein and derivatives (such as 5-bromomethyl fluorescein), Lucifer Yellow, IAEDANS, 7-Me$_2$N-coumarin-4-acetate, 7-OH-4-CH$_3$-coumarin-3-acetate, 7-NH$_2$-4-CH$_3$-coumarin-3-acetate (AMCA), monobromobimane, pyrene trisulfonates, such as Cascade Blue, and monobromorimethyl-ammoniobimane (see for example, DeLuca, *Immunofluorescence Analysis*, in *Antibody As a Tool*, Marchalonis, et al., eds., John Wiley & Sons, Ltd., (1982), which is incorporated herein by reference).

The term "linked" means covalently and non-covalently bonded, e.g., by hydrogen, ionic, or Van-der-Waals bonds. Such bonds may be formed between at least two of the same or different atoms or ions as a result of redistribution of electron densities of those atoms or ions. A polynucleotide of the invention (e.g., an oligonucleotide primer) can be linked to a detectable label and/or a solid support.

As used herein, the term "opposite orientation", when referring to primers, means that one primer comprises a nucleotide sequence complementary to the sense strand of a target polynucleotide template, and another primer comprises a nucleotide sequence complementary to the antisense strand of the same target polynucleotide template. Primers with an opposite orientation may generate a PCR amplified product from matched polynucleotide template to which they complement. Two primers with opposite orientation may be referred to as a reverse primer and a forward primer.

As used herein, the term "same orientation", means that primers comprise nucleotide sequences complementary to the same strand of a target polynucleotide template. Primers with same orientation will not generate a PCR amplified product from matched polynucleotide template to which they complement.

As used herein, a "polynucleotide" generally refers to any polyribonucleotide or poly-deoxyribonucleotide, which may be unmodified RNA or DNA or modified RNA or DNA. "Polynucleotides" include, without limitation, single- and double-stranded polynucleotides. As used herein, the term "polynucleotide(s)" also includes DNAs or RNAs as described above, that contain one or more modified bases. Thus, DNAs or RNAs with backbones modified for stability or for other reasons are "polynucleotides". The term "polynucleotides" as it is used herein embraces such chemically, enzymatically or metabolically modified forms of polynucleotides, as well as the chemical forms of DNA and RNA characteristic of viruses and cells, including for example, simple and complex cells. A polynucleotide useful for the present invention may be an isolated or purified polynucleotide or it may be an amplified polynucleotide in an amplification reaction.

As used herein, "isolated" or "purified" when used in reference to a polynucleotide means that a naturally occurring sequence has been removed from its normal cellular (e.g., chromosomal) environment or is synthesized in a non-natural environment (e.g., artificially synthesized). Thus, an "isolated" or "purified" sequence may be in a cell-free solution or placed in a different cellular environment. The term "purified" does not imply that the sequence is the only nucleotide present, but that it is essentially free (about 90-95%, up to 99-100% pure) of non-nucleotide or polynucleotide material naturally associated with it, and thus is distinguished from isolated chromosomes.

As used herein, the term "cDNA" refers to complementary or copy polynucleotide produced from an RNA template by the action of RNA-dependent DNA polymerase (e.g., reverse transcriptase). A "cDNA clone" refers to a duplex DNA sequence complementary to an RNA molecule of interest, carried in a cloning vector.

As used herein, "genomic DNA" refers to chromosomal DNA, as opposed to complementary DNA copied from an RNA transcript. "Genomic DNA", as used herein, may be all of the DNA present in a single cell, or may be a portion of the DNA in a single cell.

As used herein, "complementary" refers to the ability of a single strand of a polynucleotide (or portion thereof) to hybridize to an anti-parallel polynucleotide strand (or portion thereof) by contiguous base-pairing between the nucleotides (that is not interrupted by any unpaired nucleotides) of the anti-parallel polynucleotide single strands, thereby forming a double-stranded polynucleotide between the complementary strands. A first polynucleotide is said to be "completely complementary" to a second polynucleotide strand if each and every nucleotide of the first polynucleotide forms base-paring with nucleotides within the complementary region of the second polynucleotide. A first polynucleotide is not completely complementary (i.e., partially complementary) to the second polynucleotide if one nucleotide in the first polynucleotide does not base pair with the corresponding nucleotide in the second polynucleotide. The degree of complementarity between polynucleotide strands has significant effects on the efficiency and strength of annealing or hybridization between polynucleotide strands. This is of particular importance in amplification reactions, which depend upon binding between polynucleotide strands.

The term "expression" refers to the production of a protein or nucleotide sequence in a cell or in a cell-free system, and includes transcription into an RNA product, post-transcriptional modification and/or translation into a protein product or polypeptide from a DNA encoding that product, as well as possible post-translational modifications.

As used herein, the term "comparing the gene expression profile" refers to comparing the deferential expression of one or more polynucleotides in two or more samples.

As used herein, the term "expression profile" refers to quantitative (i.e., abundance) and qualitative expression of one or more genes in a sample.

As used herein, the term "difference in the expression profile" refers to the quantitative (i.e., abundance) and qualitative difference in expression of a gene. There is a "difference in the expression profile" if a gene expression is detectable in one sample, but not in another sample, by known methods for polynucleotide detection (e.g., electrophoresis). Alternatively, a "difference in the expression profile" exists if the quantitative difference of a gene expression (i.e., increase or decrease) between two samples is about 20%, about 30%, about 50%, about 70%, about 90% to about 100% (about two-fold) or more, up to and including about 1.2 fold, 2.5 fold, 5-fold, 10-fold, 20-fold, 50-fold or more. A gene with a difference in the expression profile between two samples is a gene which is differentially expressed in the two samples.

As used herein, the term "differential expression" refers to both quantitative, as well as qualitative, differences in a polynucleotide (e.g., a gene)'s temporal and/or cellular expression patterns among two or more samples, i.e., a difference in expression profiles. A polynucleotide is said to be "differentially expressed" if its expression is detectable in one sample, but not in another sample, by known methods for polynucleotide detection (e.g., electrophoresis). A polynucleotide is also said to be "differentially expressed" if the quantitative difference of its expression (i.e., increase or decrease) between two samples is about 20%, about 30%, about 50%, about 70%, about 90% to about 100% (about two-fold) or more, up to and including about 1.2 fold, 2.5 fold, 5-fold, 10-fold, 20-fold, 50-fold or more. A "differentially expressed" gene transcript means a mRNA transcript that is found in different numbers of copies between two or more samples, e.g., in activated versus inactivated states, in different cell or tissue types of an individual at one development stage versus another development stage, in different cell or tissue types of an individual having a selected disease compared to the numbers of copies or state of the gene transcript found in the same cells or tissues of a healthy organism. Since the number of mRNA transcript copies is proportional to the threshold cycle (Ct) the later can also be used for quantitative estimation of differential expression. Therefore the gene can be considered as differentially expressed if the difference in Ct value for gene in two different samples is more than a cycle.

As used herein, the term "abundance" refers to the amount (e.g., measured in µg, pmol or copy number) of a target polynucleotide in a sample. The "abundance" of a polynucleotide may be measured by methods well known in the art (e.g., by UV absorption, by comparing band intensity on a gel with a reference of known length and amount), for example, as described in *Basic Methods in Molecular Biology*, (1986, Davis et al., Elsevier, N.Y.); and *Current Protocols in Molecular Biology* (1997, Ausubel et al., John Weley & Sons, Inc.). One way of measuring the abundance of a polynucleotide in the present invention is to measure the fluorescence intensity emitted by such polynucleotide, and compare it with the fluorescence intensity emitted by a reference polynucleotide, i.e., a polynucleotide with a known amount.

A "polynucleotide having a nucleotide sequence encoding a gene" means a polynucleotide sequence comprising the coding region of a gene, i.e., the polynucleotide sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the vectors of the present invention may contain endogenous enhancers/promoters, splice junctions, intervening sequences, polyadenylation signals, etc. or a combination of both endogenous and exogenous control elements.

As used herein, the term "degenerate nucleotide" denotes a nucleotide which may be any of dA, dG, dC, and dT; or may be able to base-pair with at least two bases of dA, dG, dC, and dT. An unlimiting list of degenerate nucleotide which base-pairs with at least two bases of dA, dG, dC, and dT include: Inosine, 5-nitropyrole, 5-nitroindole, hypoxanthine, 6H,8H, 4-dihydropyrimido[4,5c][1,2]oxacin-7-one (P), 2-amino-6-methoxyaminopurine, dPTP and 8-oxo-dGTP.

As used herein, the term "artificial nucleotide" refers to a nucleotide which is not a naturally occurring nucleotide. The term "naturally occurring" refers to a nucleotide that exists in nature without human intervention. In contradistinction, the term "artificial nucleotide" refers to a nucleotide that exists only with human intervention. A particularly important artificial nucleotide is one which shows a preference of base pairing with another artificial nucleotide over a conventional nucleotide (i.e., dA, dT, dG, dC and dU) (e.g., as described in Ohtsuki et al. 2001, Proc. Natl. Acad. Sci., 98:4922-4925, hereby incorporated by reference). An artificial nucleotide is said to "show a preference of base pairing with another artificial nucleotide over a conventional nucleotide" when it shows 30% or more base paring ability with an artificial nucleotide as compared to any of the conventional nucleotide. The base pairing ability may be measured by the T7 transcription assay as described in Ohtsuki et al. (supra). Other unlimiting examples of "artificial nucleotides" may be found in Lutz et al. (1998) Bioorg. Med. Chem. Lett., 8:1149-1152); Voegel and Benner, (1996) Helv. Chim. Acta 76, 1863-1880; Horlacher et al. (1995) Proc. Natl. Acad. Sci., 92:6329-6333; Switzer et al. (1993), Biochemistry 32:10489-10496; Tor and Dervan (1993) J. Am. Chem. Soc. 115:4461-4467; Piccirilli et al., (1991) Biochemistry 30, 10350-10356; Switzer et al. (1989) J. Am. Chem. Soc. 111:8322-8323, all of which hereby incorporated by references. An "artificial nucleotide" may also be a degenerate nucleotide as defined hereinabove.

As used herein, a "signature sequence motif" refers to an amino acid sequence which remain highly conserved among members of a protein family or even among diverse families of proteins. These conserved residues, called "sequence motifs" or "signature sequences", can determine both protein function and structure. They are commonly used in identifying proteins or important protein regions such as active sites and binding sites. Sequence motifs are well known for many protein families. In addition, a potential sequence motif may be found by comparing related protein sequences using available computer programs.

As used herein, a "factor" refers to any substance which a cell requires to survive and/or grow and/or proliferate and which can be produced and exported by another cell. Such factors include, without limitation, growth factors (e.g., interleukins, insulin, transferrin, hydrocortisone, fibroblast growth factor, nerve growth factor, epidermal growth factor), amino acids, and vitamins.

As used herein, "solid support" means a surface to which a molecule (e.g. an oligonucleotide primer) can be irreversibly bound, including but not limited to membranes, sepharose beads, magnetic beads, tissue culture plates, silica based matrices, membrane based matrices, beads comprising surfaces including but not limited to styrene, latex or silica based materials and other polymers for example cellulose acetate, teflon, polyvinylidene difluoride, nylon, nitrocellulose, polyester, carbonate, polysulphone, metals, zeolites, paper, alumina, glass, polypropylene, polyvinyl chloride, polyvinylidene chloride, polytetrafluorethylene, polyethylene, polyamides, plastic, filter paper, dextran, germanium, silicon, (poly)tetrafluorethylene, gallium arsenide, gallium phosphide, silicon oxide, silicon nitrate and combinations thereof. A solid support according to the subject invention includes an inner wall of a reaction tube.

"Magnetic bead" means any solid support that is attracted by a magnetic field; such solid supports include, without limitation, Dynabeads, BioMag Streptavidin, MPG7 Streptavidin, Streptavidin MagnesphereJ, Streptavidin Magnetic Particles, AffiniTipJ, any of the Maga line of magnetizable particles, BioMag Superparamagnetic Particles, or any other magnetic bead to which a molecule (e.g. an oligonucleotide primer) may be attached or immobilized.

As used herein, a "modulator which regulates gene expression" refers to a compound or condition capable of either increasing or decreasing the expression of a gene (e.g., at the level of transcription) as compared to the expression of the gene in the absence of the compound or condition. As used herein, the term "condition" refers to a normal stage, a disease stage, a disease type, or a developmental stage of an individual, or an environment to which an individual is exposed. Where a difference is an increase, the increase may be as much as about 20%, about 30%, about 50%, about 70%, about 90% to about 100% (about two-fold) or more, up to and including about 5-fold, 10-fold, 20-fold, 50-fold or more. Where a difference is a decrease, the decrease may be as much as about 20%, 30%, 50%, 70%, 90%, 95%, 100% (e.g., where there is no specific protein or RNA present). The level of gene expression (e.g., at the level of transcription) may be measured by methods well known in the art, e.g., by Northern Blot, RT-PCR as described in *Basic Methods in Molecular Biology*, (1986, Davis et al., Elsevier, N.Y.); and *Current Protocols in Molecular Biology* (1997, Ausubel et al., John Weley & Sons, Inc.). The level of gene expression can also be detected by the subject methods as disclosed by the present invention. A "modulator" according to the present invention, also includes a drug or a therapeutic agent or a potential drug as defined hereinafter.

As used herein, the term "poly A site" or "poly A sequence" as used herein denotes a DNA sequence which directs both the termination and polyadenylation of the nascent RNA transcript. Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length.

As used herein, a "RNA transcript" refers to the product resulting from RNA polymerase-catalyzed transcription of a DNA sequence. When the RNA transcript is a perfect complementary copy of the DNA sequence, it is referred to as the primary transcript; or it may be an RNA sequence derived from posttranscriptional processing of the primary transcript and is referred to as the mature RNA. "Messenger RNA" (mRNA) refers to the RNA that is without introns and that can be translated into protein by the cell.

The term "drug" or "therapeutic agent" includes active fragments or analogs of a drug, e.g., a protein or a polynucleotide, that have at least 50% of the activity of the full-sized drug. A drug can be a protein, peptide, or a polynucleotide.

As defined herein, the "efficacy of a drug" or the "efficacy of a therapeutic agent" is defined as ability of the drug or therapeutic agent to restore the expression of diagnostic trait to values not significantly different from normal (as determined by routine statistical methods, to within 95% confidence levels).

A "disease or pathology" is a change in one or more biological characteristics that impairs normal functioning of a cell, tissue, and/or individual.

As used herein, the term "course of disease" or "disease stage" refers to the sequence of events in which a disease develops, causes symptoms and is either recovered from or continues and/or increases in severity.

The present invention provides a method to identify genes that are differentially expressed in two or more samples and to measure differences in their levels of expression. The present invention is based on RT-PCR using sample-specific oligonucleotide primers so those amplified products are distinguishable according to their sample sources.

The practice of the present invention will employ, unless otherwise indicated, conventional techniques of molecular biology, microbiology and recombinant DNA techniques, which are within the skill of the art. Such techniques are explained fully in the literature. See, e.g., Sambrook, Fritsch & Maniatis, 1989, *Molecular Cloning: A Laboratory Manual*, Second Edition; *Oligonucleotide Synthesis* (M. J. Gait, ed., 1984); *Polynucleotide Hybridization* (B. D. Hames & S. J. Higgins, eds., 1984); *A Practical Guide to Molecular Cloning* (B. Perbal, 1984); and a series, *Methods in Enzymology* (Academic Press, Inc.); *Short Protocols In Molecular Biology*, (Ausubel et al., ed., 1995). The practice of the present invention may also involve techniques and compositions as disclosed in U.S. Pat. Nos. 5,965,409; 5,665,547; 5,262,311; 5,599,672; 5,580,726; 6,045,998; 5,994,076; 5,962,211; 6,217,731; 6,001,230; 5,963,456; 5,246,577; 5,126,025; 5,364,521; 4,985,129. All patents, patent applications, and publications mentioned herein, both supra and infra, are hereby incorporated by reference.

Sample Sources

The invention provides for a method of detecting, measuring, and comparing the expression of a target polynucleotide in to or more samples, as defined herein. A sample according to the invention may contain at least one polynucleotide or it may be a target polynucleotide itself. Prior knowledge of sequence information of the polynucleotide may or may not be required depending on particular uses. Useful sample according to the invention includes, but is not limited to, a sample of a target polynucleotide (genomic DNA, cDNA or RNA), cell, organism, tissue, fluid, plasma, serum, spinal fluid, lymph fluid, synovial fluid, urine, tears, stool, external secretions of the skin, respiratory, intestinal and genitourinary tracts, saliva, blood cells, tumors, organs, tissue, samples of in vitro cell culture constituents, natural isolates (such as drinking water, seawater, solid materials,) microbial specimens, and objects or specimens that have been "marked" with polynucleotide tracer molecules.

Useful samples of the present invention may be obtained from different sources, including, for example, but not limited to, from different individuals, different developmental stages of the same or different individuals, different disease individuals, normal individuals, different disease stages of the same or different individuals, individuals subjected to different disease treatment, individuals subjected to different environmental factors, individuals with predisposition to a pathology, individuals with exposure to an infectious disease (e.g., HIV). Useful samples may also be obtained from in vitro cultured tissues, cells, or other polynucleotide containing sources. The cultured samples may be taken from sources including, but are not limited to, cultures (e.g., tissue or cells)

cultured in different media and conditions (e.g., pH, pressure, or temperature), cultures (e.g., tissue or cells) cultured for different period of length, cultures (e.g., tissue or cells) treated with different factors or reagents (e.g., a drug candidate, or a modulator), or cultures of different types of tissue or cells.

Samples can be obtained from an individual with a disease or pathological condition, including, but not limited to: a blood disorder, blood lipid disease, autoimmune disease, bone or joint disorder, a cardiovascular disorder, respiratory disease, endocrine disorder, immune disorder, infectious disease, muscle wasting and whole body wasting disorder, neurological disorders including neurodegenerative and/or neuropsychiatric diseases, skin disorder, kidney disease, scleroderma, stroke, hereditary hemorrhage telangiectasia, diabetes, disorders associated with diabetes (e.g., PVD), hypertension, Gaucher's disease, cystic fibrosis, sickle cell anemia, liver disease, pancreatic disease, eye, ear, nose and/or throat disease, diseases affecting the reproductive organs, gastrointestinal diseases (including diseases of the colon, diseases of the spleen, appendix, gall bladder, and others) and the like. For further discussion of human diseases, see *Mendelian Inheritance in Man: A Catalog of Human Genes and Genetic Disorders* by Victor A. McKusick (12th Edition (3 volume set) June 1998, Johns Hopkins University Press, ISBN: 0801857422), the entirety of which is incorporated herein. Preferably, samples from a normal demographically matched individual and/or from a non-disease tissue from a patient having the disease are used in the analysis to provide controls.

In one aspect, the samples are tissue or cell samples obtained from normal and individual human beings with a specific disease. Tissue samples can be obtained from cadavers or from patients who have recently died (e.g., from autopsies). Tissues also can be obtained from surgical specimens, pathology specimens (e.g., biopsies), from samples which represent "clinical waste" which would ordinarily be discarded from other procedures. Samples can be obtained from adults, children, and/or fetuses (e.g., from elective abortions or miscarriages). Cells can be obtained from suspensions of cells from tissues (e.g., from a suspension of minced tissue cells, such as from a dissected tissue), from bodily fluids (e.g., blood, plasma, sera, and the like), from mucosal scrapings (e.g., such as from buccal scrapings or pap smears), and/or from other procedures such as bronchial lavages, amniocentesis procedures and/or leukophoresis.

In some aspects, cells are cultured first prior to extracting RNAs for analysis. Cells from continuously growing cell lines, from primary cell lines, and/or secondary cell lines, also can be used.

In another aspect, the samples are tissue or cell samples obtained from normal and individual human beings carrying different diseases.

In one aspect, a plurality of tissues/cells from a single individual are obtained, i.e., the samples represent the "whole body" of an individual. Preferably, samples representing "whole body" according to the invention comprise at least five different types of tissues from a single individual. More preferably, samples representing "whole body" according to the invention comprise at least 10 or at least 15 different tissues. Tissues can be selected from the group consisting of: skin, neural tissue, cardiac tissue, liver tissue, stomach tissue, large intestine tissue, colon tissue, small intestine tissue, esophagus tissue, lung tissue, cardiac tissue, spleen tissue, pancreas tissue, kidney tissue, tissue from a reproductive organ(s) (male or female), adrenal tissue, and the like. Tissues from different anatomic or histological locations of a single organ can also be obtained, e.g., such as from the cerebellum, cerebrum, and medulla, where the organ is the brain. Some aspects of the invention comprise samples representative of organ systems (i.e., comprising samples from multiple organs within an organ system), e.g., the respiratory system, urinary system, kidney system, cardiovascular system, digestive system, and reproductive system (male or female).

In a preferred aspect, cells representing "whole body" may be obtained from tissues as described above and further comprise cells from a bodily fluid of the patient (e.g., from a blood sample).

The samples can comprise a plurality of cells from individuals sharing a trait. For example, the trait shared can be gender, age, pathology, predisposition to a pathology, exposure to an infectious disease (e.g., HIV), kinship, death from the same disease, treatment with the same drug, exposure to chemotherapy, exposure to radiotherapy, exposure to hormone therapy, exposure to surgery, exposure to the same environmental condition (e.g., such as carcinogens, pollutants, asbestos, TCE, perchlorate, benzene, chloroform, nicotine and the like), the same genetic alteration or group of alterations, expression of the same gene or sets of genes (e.g., samples can be from individuals sharing a common haplotype, such as a particular set of HLA alleles), and the like.

Although in a preferred aspect of the invention, the samples are derived from human beings, in one aspect of the invention, samples from other organisms are also used. In one aspect, the samples comprise tissues from non-human animals which provide a model of a disease or other pathological condition. When the samples represent specimens from an animal model of a chronic disease, the samples can comprise specimens representing different stages of the disease, e.g., such as from animals in a remission period or an exacerbation period. The samples can additionally, or alternatively, comprise tissues from a non-human animal having the disease or condition which has been exposed to a therapy for treating the disease or condition (e.g., drugs, antibodies, protein therapies, gene therapies, antisense therapies, combinations thereof, and the like). In some aspects, the non-human animal samples can comprise at least one cell containing an exogenous polynucleotide (e.g., the animals can be transgenic animals, chimeric animals, knockout or knockin animals).

In still further aspects, samples from plants can be used. Preferably, such samples comprise plants at different stages of their life cycle and/or comprise different types of plant tissues (e.g., at least about five different plant tissues). In one aspect, samples are obtained from plants which comprise at least one cell containing an exogenous polynucleotide (e.g., the plant can be a transgenic plant).

Isolation of mRNAs From a Sample

The subject method measures and compares the expression of a gene or genes in two or more samples. In one aspect of the invention, the expression of a gene or genes at the transcription level is measured and compared.

RNA from two or more samples to be compared (e.g., sample A and B) are extracted and individually reverse-transcribed into cDNA using sample-specific oligonucleotide primers (e.g., see FIG. 7: primers 1A and 1B).

Polynucleotides comprising RNA (e.g., mRNA) can be isolated from cells and tissues according to methods well known in the art (Ausubel et al., supra) and described below.

RNA may be purified from tissues according to the following method. Following removal of the tissue of interest, pieces of tissue of $\leq 2$ g are cut and quick frozen in liquid nitrogen, to prevent degradation of RNA. Upon the addition of a suitable volume of guanidinium solution (for example 20 ml guanidinium solution per 2 g of tissue), tissue samples are ground in a tissuemizer with two or three 10-second bursts. To prepare tissue guanidinium solution (1 L) 590.8 g guanidinium isothiocyanate is dissolved in approximately 400 ml DEPC-treated H$_2$O. 25 ml of 2 M Tris-HCl, pH 7.5 (0.05 M final) and 20 ml Na$_2$EDTA (0.01 M final) is added, the solution is stirred overnight, the volume is adjusted to 950 ml, and 50 ml 2-ME is added.

Homogenized tissue samples are subjected to centrifugation for 10 min at 12,000×g at 120 C. The resulting supernatant is incubated for 2 min at 650 C in the presence of 0.1 volume of 20% Sarkosyl, layered over 9 ml of a 5.7M CsCl solution (0.1 g CsCl/ml), and separated by centrifugation overnight at 113,000×g at 220 C. After careful removal of the supernatant, the tube is inverted and drained. The bottom of the tube (containing the RNA pellet) is placed in a 50 ml plastic tube and incubated overnight (or longer) at 40 C in the presence of 3 ml tissue resuspension buffer (5 mM EDTA, 0.5% (v/v) Sarkosyl, 5% (v/v) 2-ME) to allow complete resuspension of the RNA pellet. The resulting RNA solution is extracted sequentially with 25:24:1 phenol/chloroform/isoamyl alcohol, followed by 24:1 chloroform/isoamyl alcohol, precipitated by the addition of 3 M sodium acetate, pH 5.2, and 2.5 volumes of 100% ethanol, and resuspended in DEPC water (Chirgwin et al., 1979, *Biochemistry*, 18: 5294).

Alternatively, RNA is isolated from tissues according to the following single step protocol. The tissue of interest is prepared by homogenization in a glass teflon homogenizer in 1 ml denaturing solution (4M guanidinium thiosulfate, 25 mM sodium citrate, pH 7.0, 0.1M 2-ME, 0.5% (w/v) N-laurylsarkosine) per 100 mg tissue. Following transfer of the homogenate to a 5-ml polypropylene tube, 0.1 ml of 2 M sodium acetate, pH 4, 1 ml water-saturated phenol, and 0.2 ml of 49:1 chloroform/isoamyl alcohol are added sequentially. The sample is mixed after the addition of each component, and incubated for 15 min at 0-40 C after all components have been added. The sample is separated by centrifugation for 20 min at 10,000×g, 40 C, precipitated by the addition of 1 ml of 100% isopropanol, incubated for 30 minutes at −200 C and pelleted by centrifugation for 10 minutes at 10,000×g, 40 C. The resulting RNA pellet is dissolved in 0.3 ml denaturing solution, transferred to a microfuge tube, precipitated by the addition of 0.3 ml of 100% isopropanol for 30 minutes at −200 C, and centrifuged for 10 minutes at 10,000×g at 40 C. The RNA pellet is washed in 70% ethanol, dried, and resuspended in 100-200⊠ DEPC-treated water or DEPC-treated 0.5% SDS (Chomczynski and Sacchi, 1987, *Anal. Biochem.*, 162: 156).

Kits and reagents for isolating total RNAs are commercially available from various companies, for example, RNA isolation kit (Stratagene, La Lola, Calif., Cat # 200345); PicoPure™ RNA Isolation Kit (Arcturus, Mountain View, Calif., Cat #KIT0202); RNeasy Protect Mini, Midi, and Maxi Kits (Qiagen, Cat #74124).

In some embodiments, total RNAs are used in the subject method for subsequent analysis, e.g., for reverse transcription. In other embodiments, mRNAs are isolated from the total RNAs or directly from the samples to use for reverse transcription. Kits and reagents for isolating mRNAs are commercially available from, e.g., Oligotex mRNA Kits (Qiagen, Cat #70022).

Polynucleotides comprising RNA can be produced according to the method of in vitro transcription.

The technique of in vitro transcription is well known to those of skill in the art. Briefly, the gene of interest is inserted into a vector containing an SP6, T3 or T7 promoter. The vector is linearized with an appropriate restriction enzyme that digests the vector at a single site located downstream of the coding sequence. Following a phenol/chloroform extraction, the DNA is ethanol precipitated, washed in 70% ethanol, dried and resuspended in sterile water. The in vitro transcription reaction is performed by incubating the linearized DNA with transcription buffer (200 mM Tris-HCl, pH 8.0, 40 mM MgCl$_2$, 10 mM spermidine, 250 NaCl [T7 or T3] or 200 mM Tris-HCl, pH 7.5, 30 mM MgCl$_2$, 10 mM spermidine [SP6]), dithiothreitol, RNase inhibitors, each of the four ribonucleoside triphosphates, and either SP6, T7 or T3 RNA polymerase for 30 min at 370 C. To prepare a radiolabeled polynucleotide comprising RNA, unlabeled UTP will be omitted and $^{35}$S-UTP will be included in the reaction mixture. The DNA template is then removed by incubation with DNaseI. Following ethanol precipitation, an aliquot of the radiolabeled RNA is counted in a scintillation counter to determine the cpm/⊠ (Ausubel et al., supra).

RNAs isolated from samples are used for synthesizing cDNAs and generating amplified products for the detection and measurement of expression. In preferred embodiments, both cDNA synthesis and amplification reactions employ the use of oligonucleotide primers.

Designing Oligonucleotide Primers of the Invention

Useful oligonucleotide primers according to the invention may be designed according to general guidance well known in the art as described herein, as well as with specific requirement as described hereinafter for each steps of the subject method of the invention.

1. General Strategies for Primer Design

Oligonucleotide primers are 5 to 100 nucleotides in length, preferably from 17 to 45 nucleotides, although primers of different length are of use. Primers for synthesizing cDNAs are preferably 10-45 nucleotides, while primers for amplification are preferably about 17-25 nucleotides. Primers useful according to the invention are also designed to have a particular melting temperature (Tm) by the method of melting temperature estimation. Commercial programs, including Oligo™, Primer Design and programs available on the internet, including Primer3 and Oligo Calculator can be used to calculate a Tm of a polynucleotide sequence useful according to the invention. Preferably, the Tm of an amplification primer useful according to the invention, as calculated for example by Oligo Calculator, is preferably between about 45 and 650 C and more preferably between about 50 and 600 C.

Tm of a polynucleotide affects its hybridization to another polynucleotide (e.g., the annealing of an oligonucleotide primer to a template polynucleotide). In the subject method of the invention, it is preferred that the oligonucleotide primer used in various steps selectively hybridizes to a target template or polynucleotides derived from the target template (i.e., first and second strand cDNAs and amplified products). Typically, selective hybridization occurs when two polynucleotide sequences are substantially complementary (at least about 65% complementary over a stretch of at least 14 to 25 nucleotides, preferably at least about 75%, more preferably at least about 90% complementary). See Kanehisa, M., 1984, Polynucleotides Res. 12: 203, incorporated herein by reference. As a result, it is expected that a certain degree of mismatch at the priming site is tolerated. Such mismatch may be small, such as a mono-, di- or tri-nucleotide. Alternatively, a region of mismatch may encompass loops, which are defined as regions in which there exists a mismatch in an uninterrupted series of four or more nucleotides.

Numerous factors influence the efficiency and selectivity of hybridization of the primer to a second polynucleotide molecule. These factors, which include primer length, nucleotide sequence and/or composition, hybridization temperature, buffer composition and potential for steric hindrance in the region to which the primer is required to hybridize, will be considered when designing oligonucleotide primers according to the invention.

A positive correlation exists between primer length and both the efficiency and accuracy with which a primer will anneal to a target sequence. In particular, longer sequences have a higher melting temperature ($T_M$) than do shorter ones, and are less likely to be repeated within a given target sequence, thereby minimizing promiscuous hybridization. Primer sequences with a high G-C content or that comprise palindromic sequences tend to self-hybridize, as do their intended target sites, since unimolecular, rather than bimolecular, hybridization kinetics are generally favored in solution. However, it is also important to design a primer that contains sufficient numbers of G-C nucleotide pairings since each G-C pair is bound by three hydrogen bonds, rather than the two that are found when A and T bases pair to bind the target sequence, and therefore forms a tighter, stronger bond. Hybridization temperature varies inversely with primer annealing efficiency, as does the concentration of organic solvents, e.g. formamide, that might be included in a priming reaction or hybridization mixture, while increases in salt concentration facilitate binding. Under stringent annealing conditions, longer hybridization probes, or synthesis primers, hybridize more efficiently than do shorter ones, which are sufficient under more permissive conditions. Preferably, stringent hybridization is performed in a suitable buffer (for example, 1× RT buffer, Stratagene Catalog #600085, 1× Pfu buffer, Stratagene Catalog #200536; or 1× cloned Pfu buffer, Stratagene Catalog #200532, or other buffer suitable for other enzymes used for cDNA synthesis and amplification) under conditions that allow the polynucleotide sequence to hybridize to the oligonucleotide primers (e.g., 95° C. for PCR amplification). Stringent hybridization conditions can vary (for example from salt concentrations of less than about 1M, more usually less than about 500 mM and preferably less than about 200 mM) and hybridization temperatures can range (for example, from as low as 00 C. to greater than 220 C, greater than about 300 C, and (most often) in excess of about 370 C) depending upon the lengths and/or the polynucleotide composition or the oligonucleotide primers. Longer fragments may require higher hybridization temperatures for specific hybridization. As several factors affect the stringency of hybridization, the combination of parameters is more important than the absolute measure of a single factor.

Oligonucleotide primers can be designed with these considerations in mind and synthesized according to the following methods.

2. Oligonucleotide Synthesis

The oligonucleotide primers themselves are synthesized using techniques that are also well known in the art. Methods for preparing oligonucleotides of specific sequence are known in the art, and include, for example, cloning and restriction digest analysis of appropriate sequences and direct chemical synthesis. Once designed, oligonucleotides are prepared by a suitable chemical synthesis method, including, for example, the phosphotriester method described by Narang et al., 1979, Methods in Enzymology, 68:90, the phosphodiester method disclosed by Brown et al., 1979, Methods in Enzymology, 68:109, the diethylphosphoramidate method disclosed in Beaucage et al., 1981, Tetrahedron Letters, 22:1859, and the solid support method disclosed in U.S. Pat. No. 4,458,066, or by other chemical methods using either a commercial automated oligonucleotide synthesizer (which is commercially available) or VLSIPS™ technology.

The oligonucleotide of the subject invention may be covalently or noncovalently linked, directly or indirectly (e.g., through a linking moiety) to a solid support according to some embodiments. Oligonucleotides may be linked with the solid phase support that they are synthesized on, or they may be separately synthesized and attached to a solid phase support for use, e.g. as disclosed by Lund et al, (1988) Polynucleotides Research, 16: 10861-10880; Albretsen et al, (1990), Anal. Biochem., 189: 40-50; Wolf et al, (1987) Polynucleotides Research, 15: 2911-2926; or Ghosh et al, (1987), Polynucleotides Research, 15: 5353-5372, U.S. Pat. Nos. 5,427,779, 5,512,439, 5,589,586, 5,716,854 and 6,087,102. Methods of immobilizing a polynucleotide sequence on a solid support are also provided by the manufacturers of the solid support, e.g., for membranes: Pall Corporation, Schleicher & Schuell, for magnetic beads; Dyal, for culture plates; Costar, Nalgenunc, and for other supports useful according to the invention, CPG, Inc. Preferably, oligonucleotides are synthesized on and used with the same solid phase support, which may comprise a variety of forms and include a variety of linking moieties.

A solid substrate according to the invention is any surface to which a molecule (e.g., capture element) can be irreversibly bound, including but not limited to membranes, magnetic beads, tissue culture plates, silica based matrices, membrane based matrices, beads comprising surfaces including but not limited to styrene, latex or silica based materials and other polymers for example cellulose acetate, teflon, polyvinylidene difluoride, nylon, nitrocellulose, polyester, carbonate, polysulphone, metals, zeolites, paper, alumina, glass, polypropylene, polyvinyl chloride, polyvinylidene chloride, polytetrafluorethylene, polyethylene, polyamides, plastic, filter paper, dextran, germanium, silicon, (poly)tetrafluorethylene, gallium arsenide, gallium phosphide, silicon oxide, silicon nitrate and combinations thereof. Useful solid substrates according to the invention are also described in Sambrook et al., (1989) *Molecular Cloning: A Laboratory Manual* (2nd ed.), Vols. 1-3, Cold Spring Harbor Laboratory; Ausubel et al., supra, U.S. Pat. Nos. 5,427,779, 5,512,439, 5,589,586, 5,716,854 and 6,087,102, Southern et al., 1999, *Nature Genetics Supplement,* 21:5 and Joos et al., 1997, *Analytical Biochemistry,* 247:96. Solid phase supports for use with the invention may have a wide variety of forms, including microparticles, beads, and membranes, slides, plates, micromachined chips, and the like.

A preferred solid support of the present invention is microparticles. A wide variety of microparticle supports may be used with the invention, including microparticles made of controlled pore glass (CPG), highly cross-linked polystyrene, acrylic copolymers, cellulose, nylon, dextran, latex, polyacrolein, and the like, disclosed in the following exemplary references: *Meth. Enzmmol.*, Section A, pages 11-147, vol. 44 (Academic Press, New York, 1976); U.S. Pat. Nos. 4,678,814; 4,413,070; and 4,046;720; and Pon, Chapter 19, in Agrawal, editor, *Methods in Molecular Biology*, Vol. 20, (Humana Press, Totowa, N.J., 1993). Microparticle supports further include commercially available nucleoside-derivatized CPG and polystyrene beads (e.g. available from Applied Biosystems, Foster City, Calif.); derivatized magnetic beads; polystyrene grafted with polyethylene glycol (e.g., TentaGel.™., Rapp Polymere, Tubingen Germany); and the like. Selection of the support characteristics, such as material, porosity, size, shape, and the like, and the type of linking moiety employed depends on the conditions under which the oligonucleotides are used. For example, in applications involving successive processing with enzymes (e.g., a reverse transcriptase or a DNA polymerase), supports and linkers that minimize steric hindrance of the enzymes and that facilitate access to substrate are preferred. Other important factors to be considered in selecting the most appropriate microparticle support include size uniformity, efficiency as a synthesis support, degree to which surface area known, and optical properties, e.g. as explain more fully below, clear smooth beads provide instrumentational advantages when handling large numbers of beads on a surface.

Exemplary linking moieties for attaching and/or synthesizing oligonculeotides on microparticle surfaces are disclosed in, for example, Pon et al, (1988) Biotechniques, 6:768-775; Webb, U.S. Pat. No. 4,659,774; Barany et al, International patent application PCT/US91/06103; Brown et al, (1989) J. Chem. Soc. Commun., 1989: 891-893; Damha et al, (1990) Polynucleotides Research, 18: 3813-3821; Beattie et al, (1993) Clinical Chemistry, 39: 719-722; Maskos and Southern, (1992) Polynucleotides Research, 20: 1679-1684; and the like.

Another preferred solid support of the present invention is an inner wall of a reaction tube. The reaction tube may be made of any of cellulose acetate, teflon, polyvinylidene difluoride, nylon, nitrocellulose, polyester, carbonate, polysulphone, metals, zeolites, paper, alumina, glass, polypropylene, polyvinyl chloride, polyvinylidene chloride, polytetrafluorethylene, polyethylene, polyamides, plastic, filter paper, dextran, germanium, silicon, (poly)tetrafluorethylene, gallium arsenide, gallium phosphide, silicon oxide, or silicon nitrate. Preferably, the inner wall of a reaction tube is made of polypropylene.

Oligonucleotides may also be synthesized on a single (or a few) solid phase support to form an array of regions uniformly coated with synthesized oligonucleotides. Techniques for synthesizing such arrays are disclosed in McGall et al, International application PCT/US93/03767; Pease et al, (1994) Proc. Natl. Acad. Sci., 91: 5022-5026; Southern and Maskos, International application PCT/GB89/01114; Maskos and Southern (Supra); Southern et al, (1992) Genomics, 13: 1008-1017; and Maskos and Southern, (1993) Polynucleotides Research, 21: 4663-4669.

Preferably, the invention is implemented with oligonucleotides linked to microparticles or beads. Microparticle supports and methods of covalently or noncovalently linking oligonucleotides to their surfaces are well known, as exemplified by the following references: Beaucage and Iyer (supra); Gait, editor, *Oligonucleotide Synthesis: A Practical Approach* (IRL Press, Oxford, 1984); and the references cited above. Generally, the size and shape of a microparticle is not critical; however, microparticles in the size range of a few, e.g. 1-2, to several hundred, e.g. 200-1000 μm diameter are preferable, as they facilitate the construction and manipulation of large repertoires of oligonucleotides with minimal reagent and sample usage.

In some preferred embodiments, commercially available controlled-pore glass (CPG) or polystyrene supports are employed as solid phase supports in the invention. Such supports come available with base-labile linkers and initial nucleosides attached, e.g. Applied Biosystems (Foster City, Calif.). Preferably, microparticles having pore size between 500 and 5000 angstroms are employed.

In other preferred embodiments, non-porous microparticles are employed for their optical properties, which may be advantageously used when tracking large numbers of microparticles on planar supports, such as a microscope slide. Particularly preferred non-porous microparticles are the glycidal methacrylate (GMA) beads available from Bangs Laboratories (Carmel, Ind.). Such microparticles are useful in a variety of sizes and derivatized with a variety of linkage groups for synthesizing tags or tag complements. Preferably, for massively parallel manipulations of oligoncueltoides, microparticles of 5 μm diameter GMA beads are employed.

3. Oligonucleotide Primer Design Strategy for cDNA Synthesis

The design of a particular oligonucleotide primer for the purpose of cDNA synthesis and amplification reaction of the subject method involves selecting a sequence that is capable of recognizing and annealing to the target sequence. The Tm of the oligonucleotide is optimized by analysis of the length and GC content of the oligonucleotide.

The design of a primer useful according to the invention, may be facilitated by the use of readily available computer programs, developed to assist in the evaluation of the several parameters described above and the optimization of primer sequences. Examples of such programs are "PrimerSelect" of the DNAStar™ software package (DNAStar, Inc.; Madison, Wis.), OLIGO 4.0 (National Biosciences, Inc.), PRIMER, Oligonucleotide Selection Program, PGEN and Amplify (described in Ausubel et al., supra).

A. Compositions of Oligonucleotide Primers

An oligonucleotide primer useful according to the present invention may comprise a degenerate sequence consisting one or more degenerate bases, e.g., as described hereinafter. Such degenerate oligonucleotides will behave as normal substrates for polynucleotide kinase, DNA ligase, and other modifying enzymes (Hill, F. Loakes, D. and Brown D. M., 1998, Proc Natl Acad Sci USA., 95:4258-4263). Degenerate nucleotide can be incorporated into an oligonucleotide sequence at any position; i.e., 5', 3' or internally. Degenerated bases are known in the art and different codes are used for the description of different degeneracy (e.g., Table I).

TABLE I

| Degenerate Base Codes | |
|---|---|
| Code | Representation |
| W | A or T |
| S | G or C |
| M | A or C |
| K | G or T |
| R | A or G |
| Y | C or T |
| V | A or C or G |
| H | A or C or T |
| D | A or G or T |
| B | C or G or T |
| N | A or C or G or T |

Alternatively a degenerate base may be a nucleotide capable of base-pairing with at least two of dA, dG, dC, and dT. Such useful degenerate bases are usually nucleotide analogues and are known in the art, and as described hereinafter. For example, deoxyinosine (dI) is a naturally occurring degenerate base because it will bind to any of the four natural DNA bases. dI, while not truly universal, is less destabilizing than mismatches involving the 4 standard bases (i.e., A, T, G, and C). As used herein, "universal base" refers to a base that exhibits the ability to replace any of the four normal bases without significantly destabilizing neighboring base-pair interactions or disrupting the expected functional biochemical utility of the modified oligonucleotide. Hydrogen bond interactions between dI and dA, dG, dC, and dT are weak and unequal, with the result that some base-pairing bias does exist with dI:dC hybridization>dI:dA>dI:dG>dI:dT (Kawase, Y. et al, 1986, Polynucleotides Res., 1919:7727-7736; Martin, F. H. et. al., 1985, Polynucleotides Res., 13, 8927-8938; Case-Green, S. C., Southern, E. M., 1994, Polynucleotides Res., 22, 131-136). When present in a polynucleotide, dI preferentially directs incorporation of dC in the growing nascent strand by a DNA polymerase.

More recently, non-natural bases have been engineered that functionally are true universal bases and will not destabilize a Watson-Crick DNA duplex when paired with either dA, dG, dC, or dT. The applications of these universal DNA base analogues have been recently reviewed (Loakes, 2001, Polynucleotides Res., 29: 2437-2447). Two examples are 3-nitropyrrole 2'-deoxynucloside and 5-nitroindole 2'-deoxynucleoside (5-nitroindole). These two examples above act as truly universal bases. Other base modifications have been synthesized that are more specific. Degenerate bases which base pair with two or more, but not all four of dA, dG, dC, and dT are also useful for the subject method of the invention. Examples include the pyrimidine (C or T) analogue 6H,8H-3,4-dihydropyrimido[4,5-c][1,2]oxazin-7-one, designated as "p", and the purine (A or G) analogue N6-methoxy-2,6-diaminopurine, designated as "k". The "p" base will pair with dA or dG while the "k" base will pair with dT or dC (Bergstrom, D. E., Zhang, P., and Johnson, W. T., 1997, Polynucleotides Res. 25:1935-1942).

For example, dPTP (dP) can behave as either thymidine (T) or deoxycytidine (dC), because the base can exist in either of two tautomeric forms. In the imino-form, dP has the base-pairing properties of thymidine and so base-pairs with dA; whereas in the amino-form it mimics dC and base-pairs with dG (Sekiguchi, M., 1996, *Genes to Cells*, 1, pp. 139-145; Pavlov, Y, et al., 1994, Biochemistry, 33: 4695-4701). 8-oxo-dGTP base-pairs with either dC or dA (Sekiguchi, M., supra; Zaccolo, M., et al., 1996, J. Mol. Biol., 255: 589-603).

The oligonucleotide primers of the subject invention may comprise artificial nucleotides as defined hereinabove in the definitions. The artificial nucleotides may be located in 5', 3' or internal of an oligonucleotide primer of the subject invention. An "artificial nucleotide" may be used in an oligonucleotide so as to reduce non-specific annealing and background amplification and to increase the specificity of polynucleotide amplification. For this purpose, it is preferred that the artificial nucleotide used shows a preference of base pairing with another artificial nucleotide over a conventional nucleotide (i.e., dA, dT, dG, dC and dU). In one embodiment, one or more artificial nucleotide XTP (2-amino-6-(N,N-dimethylamino)purine 5'-Triphosphate) or YTP (Pyridin-2-one Ribonucleoside 5'-Triphosphate) are used because dXTP and dYTP exhibit base-pairing preference with each other over the conventional nucleotides, although a slight preference for dUTP also exists (Ohtsuki et al., supra).

The oligonucleotide primer of the present invention (e.g., the first oligonucleotide primer) may comprise a sequence (e.g., the sample-specific sequence tag) that is GC rich at its 5' end (i.e., a continuous stretch of nucleotides including the 5' terminal nucleotide) and AT rich as its 3' end (i.e., a continuous stretch of nucleotides including the 3' terminal nucleotide). The use of a sequence which is GC rich at 5' end and AT rich at 3' end increases the specificity of primer annealing because ATs form weaker base parings than GCs. Therefore the specificity of polynucleotide synthesis and amplification may be increased.

B. The First Oligonucleotide Primer for the First Strand cDNA Synthesis

In the subject method of the invention, a first oligonucleotide primer is used for the synthesis of the first strand cDNAs. In one embodiment, the first oligonucleotide primer is also designed with sequences that serve as templates for other primers to produce an amplification product. The first oligonucleotide primer can be between 20 and 100 nucleotides in length, preferably between 30 and 60 nucleotides in length, more preferably between 30 and 45 nucleotides in length, still more preferably between 34 and 42 nucleotides in length.

One unique feature of the instant invention is that two or more samples can be analyzed in the same reaction mixture. For this purpose, the origins of sample sources need to be properly identified. Preferably, the first oligonucleotide primer comprises a sample-specific tag. For example, the first oligonucleotide primer for synthesizing first strand cDNAs from sample A comprises a sample-specific sequence tag A; the first oligonucleotide primer for synthesizing first strand cDNAs from sample B comprises a sample-specific sequence tag B. The employment of such first oligonucleotide primer comprising a sample-specific tag provides a mechanism on which subsequence polynucleotide synthesis and amplification products can be distinguished according to their sample sources. For example, cDNAs or amplified products from sample A would comprise sample-specific tag A, which are distinguishable from cDNAs or amplified products from sample B comprising sample-specific tag B. The sample-specific sequence tag may be between 15 and 60 nucleotides in length, preferably, between 18 and 40 nucleotides in length, more preferably, between 20 and 30 nucleotides in length, still more preferably, between 20 and 24 nucleotides in length.

The sample specific sequence tag according to the invention may be a polynucleotide sequence (i.e., sample-specific sequence tag) or it may be any other identifiable tags known in the art. The sample-specific sequence tags for different first oligonucleotides (i.e., different samples) may be different in their nucleotide sequences, or they may differ simply in length.

The sample-specific tag (e.g., the sample-specific sequence tag) may be located at the 5' terminal, or 3' terminal, or both, or in the middle of the first oligonucleotides (i.e., at least one nucleotide away from the 5' terminal nucleotide and the 3' nucleotide). In a preferred embodiment, the sample-specific tag is located at the 5' terminal of the first oligonucleotide primer, i.e., there is no other nucleotide on the 5' of the sample-specific sequence.

The most majority (with the notable exception of histone mRNA) of eukaryotic mRNA are synthesized with a 3'-end "polyA" tail. The poly(A) sequence is not coded in the DNA, but is added to the RNA in the nucleus after transcription. The addition of poly(A) is catalyzed by the enzyme poly(A) polymerase, which adds ~200 A residues to the free 3'-OH end of the mRNA. The presence of 3'-end poly(A) tail has an important practical consequence. The poly(A) region of mRNA can base pair with oligo(U) or oligo(dT); and this reaction can be used to isolate poly(A)$^+$ mRNA and to synthesize cDNA from mRNA. oligo(dT) or oligo(dU) sequence can be used an a primer to prime the synthesis of the first strand cDNA using reverse transcriptase.

The first oligonucleotide primer may further comprise an oligo(dT) or oligo(dU) sequence. Preferably, the oligo(dT) or oligo(dU) sequence is located 3' of the sample-specific sequence. The oligo(dT) or oligo(dU) sequence is at least 5 nucleotide in length and may be between 5 and 20 nucleotides in length, preferably between 8 and 18 nucleotides in length, more preferably between 12 and 16 nucleotides in length.

In one embodiment, a sample-specific sequence tag comprises a general structure of about 20 to 24 nucleotides at the 5'-terminal of the first oligonucleotide primer. In a preferred embodiment, this general structure of about 20 nucleotides is followed by an oligo(dT) or oligo(dU) stretch (12-16 residues) at its at 3' end. In a preferred embodiment, the oligo(dT)

or oligo(dU) stretch is immediately 3' of the sample-specific sequence. However, there may be a non-sample-specific sequence, i.e., a common sequence for both sample A and sample B (e.g., at least one nucleotide or at least 2, or 3, or 5, or 6, or 10, or up to 20 nucleotides) between the sample-specific tag and the oligo(dT) or oligo(dU) stretch.

There is one potential problem associated with the use of oligo(dT) or oligo(dU) in cDNA synthesis. Since the polyA tail can be quite long, simply using an oligo(dT) or oligo(dU) may not accurately initiate reverse transcription right before the non-polyA region. In fact, since the oligo dT may randomly anneal to any stretch of polyA sequences, the end product of reverse transcription from even a single template mRNA can result in a heterogeneous population of 1st strand cDNA, each with a different length of polyT at the 5'-end. To overcome this problem, two more deoxynucleotides, e.g., VN, can be added to the 3'-end of the oligo(dT) or oligo(dU) primer, wherein V is any dNTP but dTTP and N is any of the four dNTPs. That way, such primer will stably anneal at the junction of the polyA tail and the non-tail region, thus ensuring uniform size of the obtained first strand cDNA synthesized from a given template. In that sense, the primer used for the first strand cDNA synthesis is in fact a degenerate oligonucleotide (Smith et al., 1997, Biotechniques 23: 274-279).

In one embodiment, the 3' terminal of the first primer further contains a degenerate sequence, i.e., a sequence comprising more than one nucleotide composition. The first oligonucleotide primer may comprise a degenerate sequence of any length, preferably less than 5 nucleotides, more preferably 2 nucleotides. In one embodiment, the degenerate sequence in the first oligonucleotide primer is VN, where V is dA, dC or dG and N is dA, dT (or dU), dC or dG. In a preferred embodiment, the first oligonucleotide primer comprises a composition of: 5'(sample-specific sequence tag)$_{20\text{-}24}$(dT)$_{12\text{-}16}$VN3'. In another embodiment, the first oligonucleotide primer comprises a composition of: 5'(sample-specific sequence tag)$_{20\text{-}24}$(dU)$_{12\text{-}16}$VN3'

The oligo(dT) or oligo(dU) stretch on the first oligonucleotide primer is annealed to complimentary (polyA)-tailed mRNAs in each sample to enable priming of first strand cDNA synthesis. The degenerate nucleotides facilitates the annealing of oligo(dT) or oligo(dU) and the efficiency of first strand cDNA synthesis. The primer-specific sequence tag is unique for each of the two samples and provides identification of the origin of the cDNA.

The use of degenerate base may result in a mixture of first oligonucleotide primers for the first strand cDNA synthesis. For example, in one embodiment the reverse transcription is conducted with a mixture of specific primers for each sample. These primers have the following structure: 5'-(specific sequence tag A)$_{20\text{-}24}$T$_{12\text{-}16}$AN-3',5'-(specific sequence tag A)$_{20\text{-}24}$T$_{12\text{-}16}$CN-3',5'-(specific sequence tag A)$_{20\text{-}24}$T$_{12\text{-}16}$GN-3' (N is a degenerated base which includes a mixture of A, T, C, G) for sample A; and 5'-(specific sequence tag B)$_{2024}$T$_{12\text{-}16}$AN-3',5'-(specific sequence tag B)$_{20\text{-}24}$T$_{12\text{-}16}$CN-3',5'-(specific sequence tag B)$_{20\text{-}24}$T$_{12\text{-}16}$GN-3' for sample B. The sample specific sequence tag need not be identical for each primer in the mixture. For example, in one embodiment the reverse transcription is conducted with a mixture of specific primers for each sample. These primers have the following structure: 5'-(specific sequence tag A1)$_{20\text{-}24}$T$_{12\text{-}16}$AN-3',5'-(specific sequence tag A2)$_{20\text{-}24}$T$_{12\text{-}16}$CN-3',5'-(specific sequence tag A3)$_{20\text{-}24}$T$_{12\text{-}16}$GN-3' (N is a degenerated base which includes a mixture of A, T, C, G) for sample A; and 5'-(specific sequence tag B1)$_{20\text{-}24}$T$_{12\text{-}16}$AN-3',5'-(specific sequence tag B2)$_{20\text{-}24}$T$_{12\text{-}16}$CN-3',5'-(specific sequence tag B3)$_{20\text{-}24}$T$_{12\text{-}16}$GN-3' for sample B.

Other nucleotide tags known in the art may be also used as sample-specific tags in the subjection invention, for example, as disclosed in Church et al, (1988, Science, 240: 185-188), Dollinger, (1994, pages 265-274 in Mullis et al, editors, *The Polymerase Chain Reaction*, Birkhauser, Boston,), Brenner and Lerner, (1992, Proc. Natl. Acad. Sci., 89: 5381-5383), Alper, (1994, Science, 264: 1399-1401), Needels et al, (1993, Proc. Natl. Acad. Sci., 90: 10700-10704) and U.S. Pat. Nos. 6,280,935, 6,172,218, 6,150,516, 5,846,719, 6,172,214, 6,235,475, all incorporated herein by references. The above patents disclose methods of tracking, identifying, and/or sorting classes or subpopulations of molecules by the use of oligonucleotide tags. The oligonucleotide tags comprising oligonucleotides selected from a minimally cross-hybridizing set can be used for sorting polynucleotides by specifically hybridizing tags attached to the polynucleotides to their complements on solid phase supports. Such oligonucleotides each consist of a plurality of subunits 3 to 9 nucleotides in length. A subunit of a minimally cross-hybridizing set forms a duplex or triplex having two or more mismatches with the complement of any other subunit of the same set. The number of oligonucleotide tags available in a particular embodiment depends on the number of subunits per tag and on the length of the subunit. Another useful nucleotide tag is disclosed by U.S. Pat. No. 6,013,445 (incorporated herein by reference) which provides a method of polynucleotide sequence analysis based on the ligation of one or more sets of encoded adaptors to the terminus of a target polynucleotide. Encoded adaptors whose protruding strands form perfectly matched duplexes with the complementary protruding strands of the target polynucleotide are ligated, and the identity of the nucleotides in the protruding strands is determined by an oligonucleotide tag carried by the encoded adaptor.

In a preferred embodiment, the first oligonucleotide primer is covalently linked to a solid support as described above herein. In this case the reverse transcription reaction generates first strand cDNAs permanently bound to the support, which allows re-using these first strand cDNAs for multiple reactions and easy separation of synthesized second strand cDNAs from the first strand cDNAs. Preferably the 5' of the first oligonucleotide primer is linked to the solid support.

In another preferred embodiment, the first oligonucleotide primer is synthesized in a solution without attaching to a solid support.

C. The Second Oligonucleotide Primer for the Second Strand cDNA Synthesis

The subject method of the invention may comprise a second strand cDNA synthesis using a second oligonucleotide primer after generating the first strand cDNAs. In this case, the synthesized second strand cDNAs or the double strand cDNAs are used as template for subsequence amplification. Alternatively, the synthesized first strand cDNAs may be directly used as templates for amplification with synthesizing the second strand cDNAs.

In one embodiment, the second oligonucleotide primer is also designed with sequences that serve as templates for other primers to produce an amplification product. The second oligonucleotide primer can be between 20 and 100 nucleotides in length, preferably between 17 and 60 nucleotides in length, more preferably between 20 and 45 nucleotides in length, still more preferably between 20 and 25 nucleotides in length. Preferably, the second oligonucleotide primer comprises a first arbitrary sequence tag. Also preferably, the second oligonucleotide primer for one sample (e.g., sample A) contains the same first arbitrary sequence tag as the second oligonucleotide primer for another sample (e.g., sample B). Because of the same first arbitrary sequence tag in second oligonucleotide primers used to synthesize second strand cDNAs from different samples, a common amplification oligonucleotide primer (e.g., the third oligonucleotide primer as described herein after) may be used for the amplification of cDNAs derived from different samples.

The first arbitrary sequence tag may be located at the 5', or 3' terminal, or internal (i.e., at least one nucleotide away from the 5' terminal nucleotide and the 3' nucleotide) of the second oligonucleotide primer. Preferably, the first arbitrary sequence tag is located at the 5' terminal, i.e., there is no other nucleotide on the 5' of the arbitrary sequence, of the second primer for second strand cDNA synthesis. The first arbitrary sequence may be between 5 and 30 nucleotides in length.

The second oligonucleotide primer may further comprise a second sequence which is complementary to a subset (i.e., a plurality) of the first strand cDNAs so as to permit the synthesis of two or more different second strand cDNAs from a sample. Preferably the second sequence is a short sequence, e.g., less than 25 nucleotides in length, preferably less than 20 nucleotides in length, more preferably less than 15 nucleotides in length, still more preferably less than 10 nucleotides in length, so as to permit its annealing to a subset of first cDNAs synthesized from a sample. In one embodiment, the second sequence of the second oligonucleotide primer is 6-7 nucleotides in length. In another embodiment, the second sequence comprises a randomly selected sequence (e.g., 6-7 base) at the 3'-end so that a subset of cDNAs are synthesized from genes (i.e., first strand cDNA) comprising a complementary sequence to the second sequence.

In general, the 3'-end of the second oligonucleotide primer is of great importance since there has to be a perfect or near perfect match at the 3'-end for a polymerase to extend from the primer. Preferably, the second sequence is located 3' of the first arbitrary sequence. In one embodiment, the second sequence is located immediately 3' of the first arbitrary sequence, i.e., there is no other nucleotide sequence between the second sequence and the first arbitrary sequence.

In a preferred embodiment, there is a third sequence located between the first arbitrary sequence and the second sequence. Preferably, the third sequence contains one or more degenerate nucleotides as described above herein. The third sequence may be between 1 and 15 nucleotides in length, preferably between 1 and 10 nucleotides in length, more preferably between 2 and 6 nucleotides in length. In one embodiment, the third sequence located between the first arbitrary sequence and the second sequence is 4 nucleotides in length (e.g., $Z_4$ in FIG. 7). The third sequence may contain all degenerate nucleotides, or it may contain a sequence of degenerated nucleotides and nondegenerate nucleotides. The degenerated nucleotide in the third sequence may be any of dA, dT, dG, and dC, or it may be a nucleotide capable of base pairing with two or more of dA, dT, dG, and dC. In a preferred embodiment, the third sequence contains four degenerated nucleotides, each of which is capable of base pairing with two or more of dA, dT, dG, and dC. In a more preferred embodiment the degenerate nucleotide is dI or 5-nitropyrrole. One purpose of including degenerate nucleotide is to increase the overall stability of the primer. It has been known that DNA polymerase will be able to read through dITP templates and randomly incorporate any of the four dNTPs when using such a dITP as template in PCR.

The selection of the second and third sequences determines what specific subsets of genes from which cDNAs are to be synthesized and amplified. By varying the second and/or third sequence, not only the size of the synthesized/amplified products can be adjusted, but also the specific gene families to be amplified can be selected. For example, small G proteins all have the signature motif of GxGxxG, wherein G is Glycine and X is any amino acid. By using degenerate oligonucleotides and matching this signature motif, expression profiles of all small G proteins can be studied. Similarly many protein families, such as kinase, phosphatase, has signature motifs and many functional domains or motifs have signature sequences (zinc finger, etc). These motifs or signature sequences are well documented and there are searchable free databases containing detailed description of these motifs/signature sequences. For example, the GCG Wisconsin Package sequence analysis tools developed by Accelrys (part of it is formerly GCG) offers such a motif search and description, the entire contents of which are hereby incorporated by reference.

In one embodiment, the second oligonucleotide comprises a general structure of 5'(first arbitrary sequence)$_{10-12}$(third sequence)$_4$(second sequence)$_{6-7}$ 3'. The use of degenerate base (e.g., any of dA, dT, dG, and dC) may result in a mixture of second oligonucleotide primers for the second strand cDNA synthesis.

The second oligonucleotide primer may or may not be linked to a solid support as described above herein. In a preferred embodiment, the second oligonucleotide is not linked to a solid support but the first oligonucleotide is so as to allow easy separation of synthesized second strand cDNAs from the first strand cDNAs which are linked to the solid support after synthesis.

To increase the specificity and to reduce the background of the cDNA synthesis and amplification reaction, when designing the first arbitrary sequence of the second oligonucleotide primer, it is preferred that its sequence does not demonstrate significant matches to sequences in any mammalian genomic sequences in GenBank database or other available databases. By "significant match", it means that there is less than 30% sequence identity (e.g., less than 20%, or less than 10%, or less than 5%, or less than 2% sequence identity) between the first arbitrary sequence and any sequence of a species, e.g., human or all mammals, available in the GenBank database or other available databases. In some embodiments, where the sample sources are known, e.g., from a particular species such as human, dog, or other animals or plants, it is preferred that the first arbitrary sequence does not demonstrate significant matches to sequences in the genomic sequences for that particular species in GenBank database or other available databases.

D. Labeling of Oligonucleotide Primers

The oligonucleotide primer of the present invention may be labeled, as described below, by incorporating moieties detectable by spectroscopic, photochemical, biochemical, immunochemical, enzymatic or chemical means. The method of linking or conjugating the label to the oligonucleotide primer depends, of course, on the type of label(s) used and the position of the label on the primer. A primer that is useful according to the invention can be labeled at the 5' end, the 3' end or labeled throughout the length of the primer.

A variety of labels that would be appropriate for use in the invention, as well as methods for their inclusion in the primer, are known in the art and include, but are not limited to, enzymes (e.g., alkaline phosphatase and horseradish peroxidase) and enzyme substrates, radioactive atoms, fluorescent dyes, chromophores, chemiluminescent labels, electrochemiluminescent labels, such as Origen™ (Igen), that may interact with each other to enhance, alter, or diminish a signal. Of course, if a labeled molecule is used in a PCR based assay carried out using a thermal cycler instrument, the label must be able to survive the temperature cycling required in this automated process.

Fluorophores for use as labels in constructing labeled primers of the invention include rhodamine and derivatives (such as Texas Red), fluorescein and derivatives (such as 5-bromomethyl fluorescein), Lucifer Yellow, IAEDANS, 7-Me$_2$N-coumarin-4-acetate, 7-OH-4-CH$_3$-coumarin-3-acetate, 7-NH$_2$-4-CH$_3$-coumarin-3-acetate (AMCA), monobromobimane, pyrene trisulfonates, such as Cascade Blue, and monobromorimethyl-ammoniobimane. In general, fluorophores with wide Stokes shifts are preferred, to allow using fluorimeters with filters rather than a monochromometer and to increase the efficiency of detection.

The labels may be attached to the oligonucleotide directly or indirectly by a variety of techniques. Depending on the precise type of label or tag used, the label can be located at the 5' end of the primer or located internally in the primer, or attached to spacer arms of various sizes and compositions to facilitate signal interactions. Using commercially available phosphoramidite reagents, one can produce oligomers containing functional groups (e.g., thiols or primary amines) at the 5'-terminus via an appropriately protected phosphoramidite, and can label them using protocols described in, for example, *PCR Protocols: A Guide to Methods and Applications*, Innis et al., eds. Academic Press, Ind., 1990.

Methods for introducing oligonucleotide functionalizing reagents to introduce one or more sulfhydryl, amino or hydroxyl moieties into the oligonucleotide primer sequence, typically at the 5' terminus, are described in U.S. Pat. No. 4,914,210. A 5' phosphate group can be introduced as a radioisotope by using polynucleotide kinase and gamma-$^{32}$P-ATP or gamma-$^{33}$P-ATP to provide a reporter group. Biotin can be added to the 5' end by reacting an aminothymidine residue, or a 6-amino hexyl residue, introduced during synthesis, with an N-hydroxysuccinimide ester of biotin.

Synthesis of cDNAs cDNAs may be prepared and used for amplification according to the subject method of the invention. In some embodiments, first strand cDNAs are prepared and used directly for subsequence amplification reaction and analysis. In preferred embodiments of the invention, both first and second cDNAs are synthesized. The synthesized first and second strand cDNAs may be used for subsequent amplification reactions or the second strand cDNAs may be separated from the first strand cDNAs and used for amplification reactions.

The preparation of cDNA is well-known and well-documented in the art (e.g., Ausubel et al., supra) and as described below.

cDNA may be prepared according to the following method. Total cellular RNA is isolated (as described) and passed through a column of oligo(dT) or oligo(dU)-cellulose to isolate polyA RNA. The bound polyA mRNAs are eluted from the column with a low ionic strength buffer. To produce cDNA molecules, first oligonucleotide primers comprising oligo(dT)n or oligo(dU)n as described above herein (where n is preferably 12-16 nucleotides in length) are hybridized to the polyA tails to be used as primers for reverse transcriptase, an enzyme that uses RNA as a template for DNA synthesis. Alternatively, mRNA species are primed from many positions by using short oligonucleotide fragments comprising numerous sequences complementary to the mRNA of interest as primers for cDNA synthesis. The resultant RNA-DNA hybrid (i.e., RNA and first strand cDNA) is converted to a double stranded DNA molecule (i.e., first and second strand cDNA) by a variety of enzymatic steps well-known in the art (Watson et al., 1992, *Recombinant DNA*, 2nd edition, Scientific American Books, New York).

In one aspect of the invention, the first strand cDNAs are synthesized using an oligonucleotide primer comprising a sample-specific sequence, so that the synthesized first strand cDNAs are identifiable as to their sample sources. The oligonucleotide primer used for first strand cDNA synthesis, therefore, comprises at least an oligo(dT) or oligo(dU) sequence and a sample-specific sequence.

In one embodiment, the first strand cDNAs for sample A are synthesized using mRNAs isolated from sample A and an oligonucleotide primer comprising a sample A-specific sequence. The first strand cDNAs for sample B are synthesized using mRNAs isolated from sample B and an oligonucleotide primer comprising a sample B-specific sequence. The sample A-specific sequence may be different from the sample B-specific sequence by comprising different nucleotide identities and/or it may be different from sample B-specific sequence by comprising a different length of nucleotides.

In a preferred embodiment, the first oligonucleotide primer is linked to a solid support, for example, on beads via covalent links. This is advantageous since once synthesized on beads, these first strand cDNA can be easily washed and purified away from excessive reagents so that a direct use of these beads in a separate reaction is possible. Secondly, after second strand cDNA synthesis (see below), these bound first strand cDNAs can be separated from the second strand cDNAs by denaturing the double strand DNA so that they can be used for other related or unrelated experiments, fro example the separated second strand cDNAs can be amplified by subsequent amplification reaction.

Preferably, the synthesis of the first strand cDNA is a reverse transcription reaction. The first strand cDNA is prepared by contacting the RNA sample with the first oligonucleotide primer and requisite reagents under conditions sufficient for reverse transcription of the RNA template in the sample. Requisite reagents contacted with the primers and RNAs are known to those of skill in the art and will generally include at least an enzyme having reverse transcriptase activity and dNTPs in an appropriate buffer medium.

A variety of enzymes, usually DNA polymerases, possessing reverse transcriptase activity can be used for the first strand cDNA synthesis step. Examples of suitable DNA polymerases include the DNA polymerases derived from organisms selected from the group consisting of a thermophilic bacteria and archaebacteria, retroviruses, yeasts, Neurosporas, Drosophilas, primates and rodents. Preferably, the DNA polymerase will be selected from the group consisting of Moloney murine leukemia virus (M-MLV) as described in U.S. Pat. No. 4,943,531 and M-MLV reverse transcriptase lacking RNaseH activity as described in U.S. Pat. No. 5,405,776 (the disclosures of which patents are herein incorporated by reference), Avian myeloblastosis virus (AMV), human T-cell leukemia virus type I (HTLV-I), bovine leukemia virus (BLV), Rous sarcoma virus (RSV), human immunodeficiency virus (HIV) and *Thermus aquaticus* (Taq) or *Thermus thermophilus* (Tth) as described in U.S. Pat. No. 5,322,770, the disclosure of which is herein incorporated by reference, as well as BcaBEST™ DNA Polymerase as described in U.S. Pat. No. 5,436,149 (the disclosure of which is herein incorporated by reference). Suitable DNA polymerases possessing reverse transcriptase activity may be isolated from an organism, obtained commercially or obtained from cells which express high levels of cloned genes encoding the polymerases by methods known to those of skill in the art, where the particular manner of obtaining the polymerase will be chosen based primarily on factors such as convenience, cost, availability and the like.

The various dNTPs and buffer medium necessary for first strand cDNA synthesis through reverse transcription of the primed RNAs may be purchased commercially from various sources, where such sources include Clontech, Sigma, Life Technologies, Amersham, Boehringer-Mannheim. Buffer mediums suitable for first strand synthesis will usually comprise buffering agents, usually in a concentration ranging from 10 to 100 µM which typically support a pH in the range 6 to 9, such as Tris-HCl, HEPES-KOH, etc.; salts containing monovalent ions, such as KCl, NaCl, etc., at concentrations ranging from 0-200 mM; salts containing divalent cations like MgCl.sub.2, Mg(OAc) etc, at concentrations usually ranging from 1 to 10 mM; and additional reagents such as reducing agents, e.g. DDT, detergents, albumin, polyalcohols (glycerol) and the like. The conditions of the reagent mixture will be selected to promote efficient first strand synthesis. Typically the primer will first be combined with the RNA sample at an elevated temperature, usually ranging from 50 to 95° C., followed by a reduction in temperature to a range between about 0 to 60° C., to ensure specific annealing of the primers to their corresponding RNAs in the sample. Following this annealing step, the primed RNAs are then combined with dNTPs and reverse transcriptase under conditions sufficient to promote reverse transcription and first strand cDNA synthesis of the primed RNAs. By using appropriate types of reagents, all of the reagents can be combined at once if the activity of the polymerase can be postponed or timed to start after annealing of the primer to the RNA.

In some embodiments, the first strand cDNAs are used as template for the synthesis of second strand cDNAs.

Optionally, RNAs may be removed before the synthesis of second strand cDNA by either RNase H digestion or by treatment with 0.1-1M NaOH.

Since the expression profile of any given sample can be quite complicated and the resolution of any system is limited to certain extend, it is beneficial to selectively amplify a subset, rather than the whole set, of expressed gene. This can also be useful since in certain situations, only a given subset of genes might be of interest and it will be beneficial to filter out other genes not of interest to improve signal-to-noise ratio. If, however, an analysis of the complete genome is desired, multiple runs using different primer sets can be easily achieved if the first strand cDNA is bound to a solid support (see above). Therefore, the identity of the second strand primer (i.e., the second oligonucleotide primer) will define which subset of expressed genes gets amplified.

The second strand cDNA is annealed to the first strand cDNA and forms a complete double stranded DNA copy of the original mRNA.

The composition of second oligonucleotide primer defines the subset of all expressed genes that will be synthesized. In general, the 3'-end of the primer as described herein above, which is most important for DNA polymerase priming, contains a short sequence (for example, a 6-7 bp sequence) which serves to select the cDNA molecules to be synthesized.

The occurrence of such short 3'-end priming sequences in expressed portion of mammalian genome can be estimated. For example, if a 6 bp palindromic sequence is used, depending on particular sequence used, about 5,000-10,000 occurrence are expected using current mouse sequence data (e.g. $1.5 \times 10^8$ bases in sequenced mouse cDNAs). Since particular cells and tissues express only a portion of all genes in the total genome (10-30%), and because under commonly used PCR conditions transcripts longer than 2,000 bases are unlikely to be amplified, 500-2,000 individual transcripts are expected to be detected. It is estimated that in a single reaction using such primers, about 5-10% of the expressed genome (5,000/1.5× $10^8$ (frequency)×2,000 (size of amplifiable fragment)× 100=6.7%) can be covered. Therefore, it is anticipated that about 20 separate reactions (using the same genetic sample) should cover a considerable portion of all transcribed sequences in a single mammalian genome.

Certain bases not commonly found in natural polynucleotides may be included in the polynucleotides of the present invention and include, for example, inosine and 7-deazaguanine. Complementarity need not be perfect; stable duplexes may contain mismatched base pairs or unmatched bases. Those skilled in the art of polynucleotide technology can determine duplex stability empirically considering a number of variables including, for example, the length of the oligonucleotide, base composition and sequence of the oligonucleotide, ionic strength, and incidence of mismatched base pairs.

Stability of a polynucleotide duplex is measured by the melting temperature, or "$T_m$". The $T_m$ of a particular polynucleotide duplex under specified conditions is the temperature at which half of the base pairs have disassociated. The melting temperature of a double strand DNA molecule depends markedly on its base composition. DNA molecules rich in GC base pairs have a higher Tm than those having an abundance of AT base pairs. The dependence of $T_m$ on base composition is linear, increasing about 0.4° C. for every percent increase in G-C content. GC base pairs are more stable than AT pairs because their bases are held together by three hydrogen bonds rather than by two. In addition, adjacent GC base pairs interact more strongly with one another than do adjacent AT base pairs. Hence, the AT-rich regions of DNA are the easier to melt.

A major effect on $T_m$ is exerted by the ionic strength of the solution. The $T_m$ increases 16.6° C. for every tenfold increase in monovalent cation concentration. The most commonly used condition is to perform manipulations of DNA in 0.12 M phosphate buffer, which provides a monovalent Na$^+$ concentration of 0.18M, and a $T_m$ of the order of 90° C. The $T_m$ can be greatly varied by performing the reaction in the presence of reagents, such as formamide, that destabilize hydrogen bonds. This allows the $T_m$ to be reduced to as low as 40° C. with the advantage that the DNA does not suffer damage (such as strand breakage) that can result from exposure to high temperatures. (Stryer, *Biochemistry*, 1998, 3$^{rd}$ Edition, W.H. Freeman and Co., pp. 81-82 and Lewin, *Genes II*, 1985, John Wiley & Sons, p. 63-64).

The synthesized second strand cDNAs can be optionally separated from the first strand cDNAs synthesized linked to a solid support. The bound first strand cDNAs can then be isolated and used later in other reactions. Alternatively, these bound double strand cDNAs can be used directly in subsequent PCR.

In one embodiment, the newly synthesized second strand cDNAs is separated from the bound first strand cDNAs by, for example, exposing cDNAs to a denaturing temperature, i.e. a temperature higher than Tm. The bound first strand cDNAs can then be reused for further analysis, by using a different oligonucleotide primer to generate a new pool of second strand cDNAs for analysis.

Alternatively the specific pool of cDNA fragments can be generated by enzymatic digestion of the double stranded DNA by the action of an appropriate restriction enzyme (e.g. recognizing the introduced palindromic site) and by the ligation of the specific adapter which contains a specific sequence "C" and 5' end and a single-stranded overhand compatible with the overhand generated by the restriction enzyme.

Amplification

Synthesized cDNAs (e.g., first strand, or second strand or double strand) are used to generate amplified products for analysis. In the subject invention, PCR amplification is preferred although other amplification methods known in the art can also be used (e.g., LCR, and NSBA).

PCR methods are well-known to those skilled in the art, such as described in Mullis and Faloona, 1987, Methods Enzymol., 155: 335, Saiki et al., 1985, *Science* 230:1350, and U.S. Pat. Nos. 4,683,202, 4,683,195 and 4,800,159, herein incorporated by reference. In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of $10^9$.

In the present invention, PCR is performed using template DNA, i.e., cDNA (at least 1 fg; more usefully, 1-1000 ng) and at least 25 pmol of oligonucleotide primers (i.e., the third and fourth oligonucleotide primer). For example, a typical reaction mixture includes: 1-1000 pg of cDNA, 25-100 pmol of oligonucleotide primer, 2.5-10 ⊠l of a suitable 10× buffer, 0.4-2 ⊠l of 10 ⊠M dNTP, 2.5 units of Taq DNA polymerase and deionized water to a total volume of 25-100 ⊠l. Mineral oil may be overlaid and the PCR is performed using a programmable thermal cycler.

Preferably, the third oligonucleotide primer comprises the sample-specific sequence of the first oligonucleotide primer. In a preferred embodiment, the third oligonucleotide primer comprises the whole or a portion of the sample-specific sequence and is capable of annealing to its complementary sequence (i.e., in second cDNAs). This embodiment preferably also employees a fourth oligonucleotide primer (i.e., with opposite orientation to the third oligonucleotide primer). Preferably, this fourth oligonucleotide primer comprises the first arbitrary sequence of the second oligonucleotide primer. If the second strand cDNAs of different samples are synthesized using the same second oligonucleotide, the same fourth oligonucleotide primer may be used to the amplification of the cDNAs by PCR.

The use of the third oligonucleotide primer comprising a sample-specific sequence ensures the amplified products can be identified according to their sample origins without losing track of their identity.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 300 C and 720 C is used. Initial denaturation of the template molecules normally occurs at between 920 C and 990 C for 4 minutes, followed by 20-40 cycles consisting of denaturation (94-990 C for 15 seconds to 1 minute), annealing (temperature determined as discussed above; 1-2 minutes), and extension (720 C for 1-3 minutes). Preferably, the amplified products are labeled with detectable labels so that their identity and abundance may be detected. Detectable labels as defined herein above (e.g., fluorescent, radioactive, or colorimetric labels) may be linked to the amplified products by various means. For example, a dNTP may be labeled which leads to the labeling of an amplified polynucleotide once the dNTP is incorporated into the Polynucleotide. Alternatively, a primer used for amplification may be labeled which also leads to the labeling of an amplified Polynucleotide. In addition, a labeled probe (e.g., an oligonucleotide complementary to an amplified product) may be used to hybridize to the amplified product therefore generating a detectable signal with the amplified product (i.e., in a hybridization assay).

In a preferred embodiment, the 5'-end of each sample-specific PCR primer (i.e., the third oligonucleotide primer) is linked to a specific fluorescent label so that the lineage of the PCR product can be easily traced by their fluorescent marker according to the sample origin. In addition, the strength of the fluorescent signal is directly proportional to the amount of the PCR product. By recording the fluorescent strengths of a given product, a ratio between PCR products of different origin can be obtained.

Although each sample preferably has its specific fluorescent label, the same fluorescent label can be used by more than one sample. For example, if the fluorescin-tagged third oligonucleotide primer for sample A is 1 base shorter (or longer) than that of sample B, and if the separation means is sensitive enough to detect 1 bp difference, then the "same" PCR fragment originating from these two samples will be resolved as two close peaks differing in size by 1 bp (e.g., by denaturing high performance liquid chromatography (DH-PLC)). The same recording and calculation can then be effectuated if the size difference is accounted for. The same strategy may be useful for more than 2 samples.

Although fluorescent label is the preferred label, other labels can also be used to achieve the same purpose. If the lab is isotope with different molecular weights (i.e. P31 vs. P32 vs. P33; O16 vs. O18, etc), primer for sample A may be "heavier" than primer for sample B. Such difference may result in the PCR product of different origin to be separated by a detectable margin, for example, on mass spectrometry, so that a ratio can be calculated based on these closely related peaks.

Figure 3:
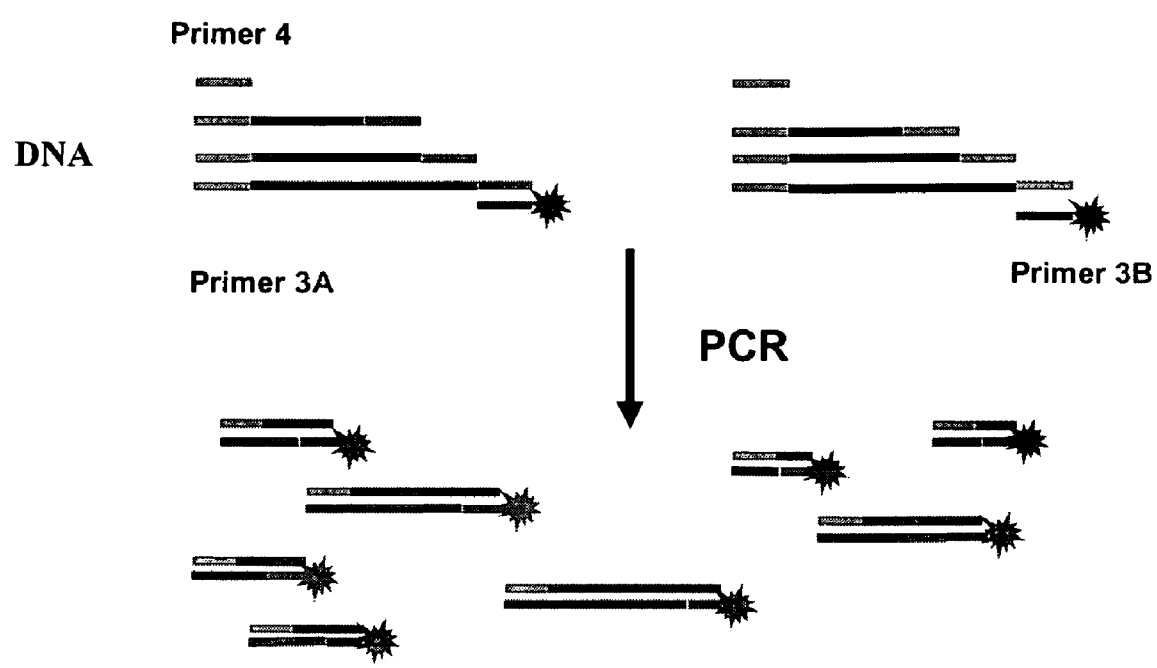
FIG. 3 is a diagram showing the PCR amplification to generate amplified products with sample-specific tags according to one embodiment of the invention.

In one embodiment, the collected cDNA prepared from two or more samples are combined and subjected to PCR amplification using two pairs of primers (FIG. 3). Primer 4 is a common primer and it is either identical to primer 2, or identical to the 5'-end unique sequence in primer 2. Primers 3A and 3B are identical to the sample-specific tag sequences incorporated into DNA during reverse transcription. In addition each of these primers contains specific fluorescent label at the 5'-end of the primer. That will ensure that the PCR products resulting from these two separate samples will be separately labeled by different sample-specific fluorophors, even though PCR is carried out in the same reaction mixture. The primers 3A and 3B can represent a mixture of corresponding primers 3A1, 3A2, 3A3 and 3B 1, 3B2, 3B3 identical to the specific sequences A1, A2, A3 and B1, B2, B3 which were introduced during the reverse transcription reaction. Each of these primers may contain a unique fluorescent dye.

The use of a primer mixture instead of a single primer for each sample will increase the number of genes that could be analyzed in a single reaction. Since specific sequences A1-A3 and B1-B3 are incorporated depending on the nucleotide preceding polyA tail in the mRNA and the products of their amplification appear in different fluorescent channels, this method can distinguish between DNA fragments that have similar size but differ in the nucleotide preceding polyA sequence.

In some embodiments of the invention, a nested amplification is performed using amplified products in a preceding amplification reaction as templates. The use of nested PCR can also greatly enhance the yield of the species-specific product, therefore the sensitivity of the assay, when a single primer pair fails by itself. Preferably, one of the nested PCR primer contains a sample-specific sequence so as to keep tracking the sample origin of the amplified product. Also preferably, the primer containing the sample-specific sequence is labeled with specific detectable label to permit the detection and analysis of amplified products. For example, a method comprising a nested PCR involves two sequential PCR reactions. After multiple cycles of PCR (e.g., 10 to 40, or 10 to 30 or 10 to 20 cycles) with the first pair of primers (e.g., with the third and the fourth oligonucleotide primers), a small amount aliquot of the first reaction (e.g., 1 µl of a 50 µl reaction) serves as the template for a second multiple cycles of PCR reaction (e.g., 10 to 40, or 10 to 30 or 10 to 20 cycles) with a new set of primers that anneal to sequences internal to, or nested between, the first pair.

Methods for designing nested primers and for performing nested PCR are known in the art (See *Current Protocol in Molecular Biology*, supra). The general criteria for selecting primers as described above also apply to the design of nested primers. Both nested primers need to anneal to sequences internal to (e.g., within) the first pair of primers and at least one of the nested primers, however, according to the subject invention, needs to be contain a sample-specific sequence.

Separation and Detection of Amplified Products

During PCR amplification, starting from a predetermined time or cycle (for example, the $5^{th}$ cycle, or the $8^{th}$ cycle, or the $10^{th}$ cycle or other cycle), an aliquot, e.g., between 1% to 40% (v/v) of the reaction mixture, is automatically withdrawn after each cycle, and the reaction mixture is replenished with equal volumes of fresh components such as dNTP, fluorescent labeled primers and DNA polymerase. The withdrawn sample is then separated and analyzed. Methods for detecting the presence or abundance of polynucleotides are week known in the art and any of them can be used in the subject method of the invention so long as they are capable of separates individual polynucleotides although it is preferred that quantitative analysis can be performed simultaneously. Useful methods for the separation and analysis of the amplified products include, but are not limited to, electrophoresis (e.g., capillary electrophoresis (CE)), chromatography (dHPLC), and mass spectrometry.

In one embodiment, CE is a preferred separation means since it provides exceptional separation of the polynucleotides in the range of at least 10-1,000 base pairs with a resolution of a single base pair. CE can be performed by method well known in the art, for example, for example, as disclosed in U.S. Pat. Nos. 6,217,731; 6,001,230; and 5,963,456, incorporated herein by reference. Recently developed throughput CE apparatuses are available commercially, for example, the HTS9610 High throughput analysis system and SCE 9610 fully automated 96-capillary electrophoresis genetic analysis system from Spectrumedix Corporation (State College, Pa.); P/ACE 5000 series and CEQ series from Beckman Instruments Inc (Fullerton, Calif.); and ABI PRISM 3100 genetic analyzer (Applied Biosystems, Foster City, Calif.). Near the end of the CE column, the amplified DNA fragments will pass a fluorescent detector which measures signals of both fluorescent labels. These apparatuses provide automated high throughput for the detection of fluorescence-labeled PCR products.

The employment of CE in the subject method permits higher productivity compared to conventional slab gel electrophoresis. The separation speed is limited in slab gel electrophoresis because of the heat produced when the high electric field is applied to the gel. Since heat elimination is very rapid from the large surface area of a capillary, a higher electric field can be applied to capillary electrophoresis, thus speeding up the separation process. By using a capillary gel, the separation speed is increased about 10 fold over conventional slab-gel systems.

With CE, one can analyze multiple samples at the same time which is essential for high-throughput. This is achieved by employing multi-capillary systems in one embodiment of the invention. However, the detection of fluorescence from DNA bases may be complicated by the scattering of light from the porous matrix and capillary walls. A confocal fluorescence scanner may be used to avoid light scattering (Quesada et al., 1991, Biotechniques 10:616-25).

In one embodiment, the subject method measures how many copies of a particular cDNA (i.e., mRNA) contained in the original sample used as template for PCR amplification. To determine the number of original copies, the efficiency of the nucleic acid extraction, as well as the efficiency of each PCR reaction must be known. Further, the detection step reveals how many copies of the target sequence have been made, but not how many copies were contained in the original sample.

Figure 4:
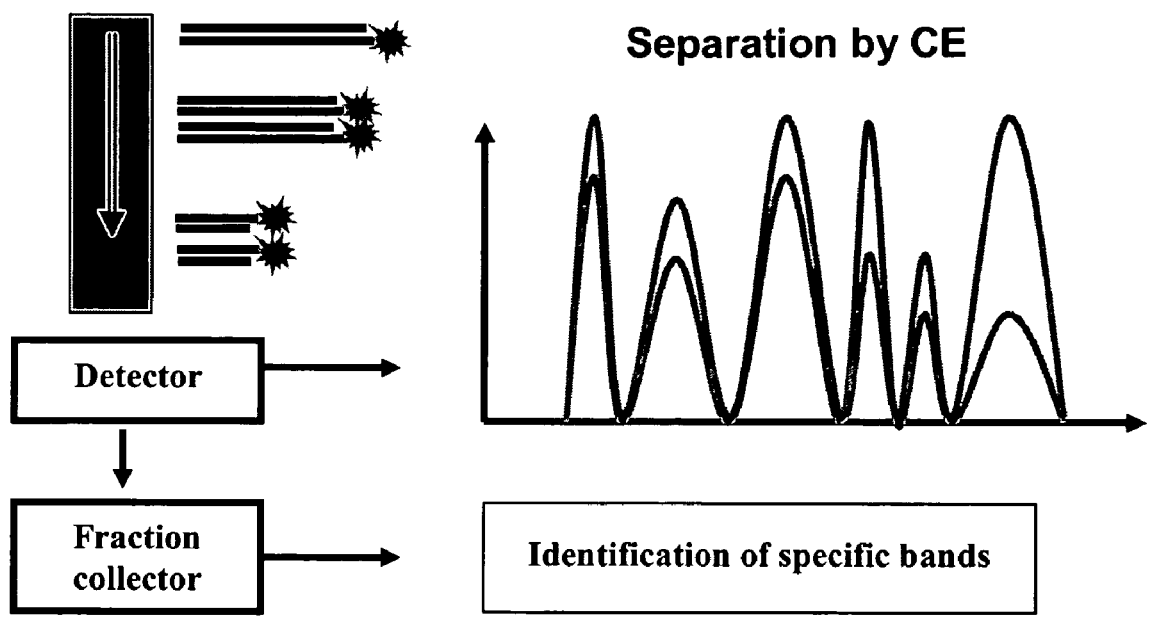
FIG. 4 is a diagram showing the separation and analysis of PCR products according to one embodiment of the invention.

In a preferred embodiment, differences in gene expression, rather than the exact numbers of copies of the target sequence contained in the sample is measured. The detected fluorescent signal strength (e.g., following CE separation) can be recorded and used to determine the relative ratio of each peak from the two samples (FIG. 4). In a preferred embodiment, cDNAs derived from two or more samples are amplified in the same PCR reaction. Each sample is amplified by a common primer (e.g., the fourth oligonucleotide primer) and a sample specific primer, therefore cDNAs from different samples will compete for the same common primer. Because of this competition, the ratio of the amounts of the amplified products from two samples reflects the ratio of the amounts of the initial target polynucleotide in each of the two samples. For example, a ratio (e.g., sample A/sample B) of 1 indicates that same initial amount of the target polynucleotide in the samples A and B, i.e., that the target polynucleotide is not differentially expressed in the two samples. A ratio of greater than 1 (e.g., sample A/sample B) indicates a higher amount of the target polynucleotide in sample A than in sample B. A ratio of smaller than 1 (e.g., sample A/sample B) indicates a less amount of the target polynucleotide in sample A than in sample B. In both of the above cases, the target polynucleotide is differentially expressed in the two samples. It is expected that the amount of majority polynucleotides present in two samples (i.e., the expression level of these polynucleotides) are about the same therefore the ratio of amplification will remain constant (e.g., at about 1).

Figure 5:
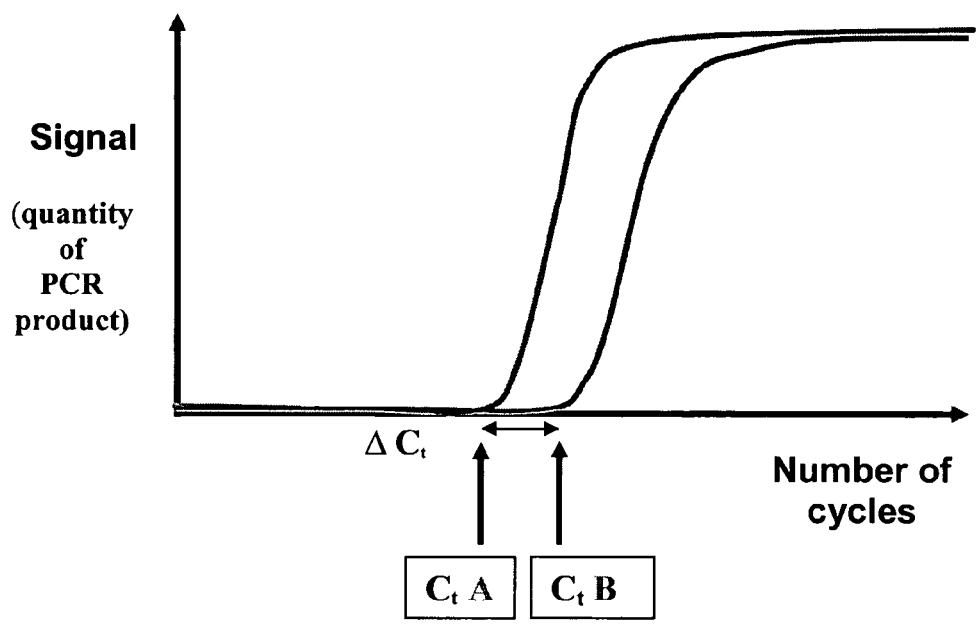
FIG. 5 is a graph showing typical curves of PCR product accumulation according to one embodiment of the invention. It is apparent that the range of cycles where differences between different samples are most easily detected is narrow. a) The quantitative measure of gene expression (Ct) is defined as a cycle number corresponding to the point at which the signal intensity exceeds the chosen threshold limit (usual set as 10 fold the standard deviation of the baseline). The operational differential expression ($\Delta$Ct) is defined as difference in Ct values for two PCR fragments. b) Alternative determination of threshold cycle based on plotting of d(Signal intensity)/d(cycle number) as a function of cycle number. The alternative determination of threshold cycle (aCt) is defined as a cycle number which corresponds to the maximal value of d(Signal intensity)/d(cycle number). Similar to threshold number, aCt can be used to determine absolute copy number for each gene (log(copy number)=AaCt+B). The alternative operational differential expression ($\Delta$aCt) is defined as difference in aCt values for two PCR fragments.
Figure 5:
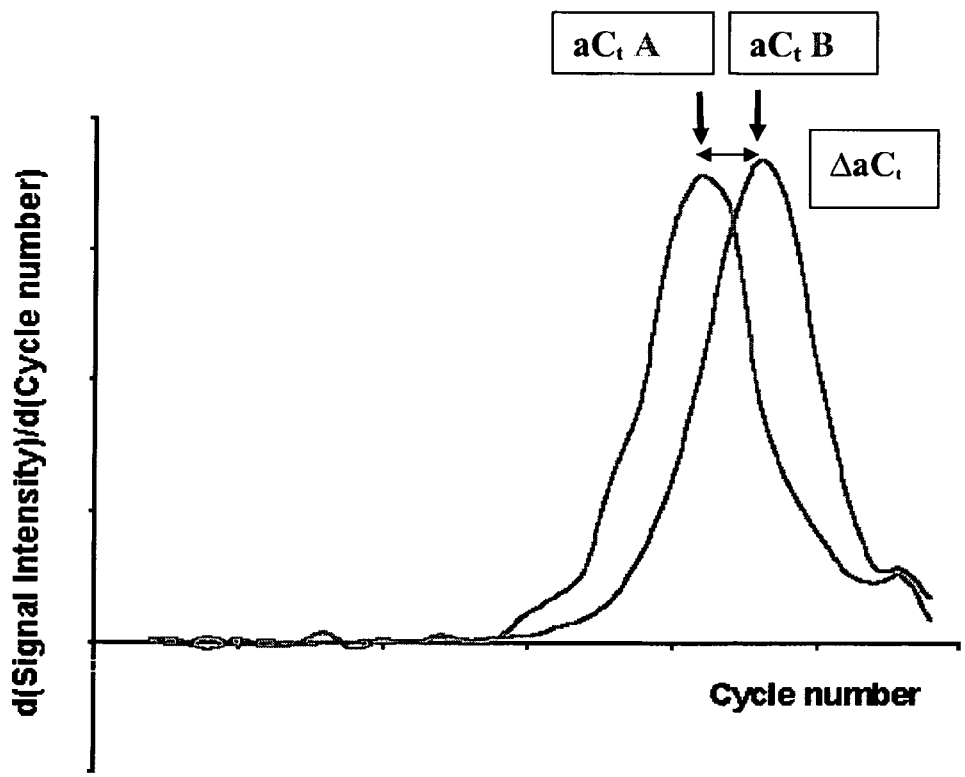

In another preferred embodiment the signal intensity for each PCR fragment (and therefore for each gene) separated by CE will be plotted as a function of cycle number. The signal intensity can be represented by total area of peak on the electrophoregram. A threshold cycle number (Ct) will be calculated as a cycle number at which signal intensity of PCR fragment will reach a set threshold value (for example 10 standard deviations of background value of signal intensity) for each amplified gene. Operational differential expression of particular gene is determined as a difference in threshold cycle number (Ct) for this gene in two (or more) samples more than one cycle in value. The threshold cycle number is further used to derive copy number for each gene and to measure the difference in the expression by a ratio of copy numbers for gene in two or more samples (FIG. 5a).

The method also comprises generating an plot of the rate of signal intensity change as a function of number of amplification cycles [derivative of Signal Intensity as a function of cycle numer, d(Signal Intensity)/d(cycle number)] for each amplified gene. The alternative threshold cycle (aCt), determined as a cycle number corresponding to the maximal value of d(Signal Intensity)/d(cycle number) for each amplified gene from one sample, is compared to the aCt for the same gene from another sample. Difference in one cycle between aCt values for the same gene in two or more samples is defined as alternative operational differential expression (FIG. 5b).

Also preferably, the method further comprises collecting PCR fragment or PCR fragments corresponding to one or more genes which display operational differential expression or alternative operational differential expression, and identifying the sequence of the one or more genes.

The ratio of a particular polynucleotide in two samples may be further measured against a common ratio for determining whether it is differentially expressed between the two samples. The term "common ratio" as used herein means a relatively constant ratio of all genes expressed between two samples. It reflects a global change (amount of total starting material) rather than a specific change caused by certain events such as activation of a particular signal transduction pathway in a treated sample as compared to an untreated sample. By comparing ratio of expression of a particular gene with this common ratio, it will be immediately apparent whether the expression of that particular gene is different between the samples being compared.

If the two samples are amplified in separate PCR reactions, an internal control may be provided for each PCR amplification and the amplification of each sample is first normalized according to internal control before the ratio is calculated. The use of internal control for quantitative PCR is well-known in the art, for example, as described in Ausubel et al. There are two basic types of control: the first is commonly known as exogenous control (Gilliland et al. (1990) PCR Protocols, Innis et al. ed., pp. 60-69, Academic Press; Wang et al. (1989) Proc. Natl. Acad. Sci. USA 86:9717-9721, both of which are specifically incorporated herein by reference), and the second, is known as endogenous control (Dveksler et al. (1992) PCR Methods and Applications 6:283-285; Spanakis (1993) Nucleic Acids Research 21:3809-3819, both of which are specifically incorporated herein by reference).

Exogenous control involves the use of an artificially introduced nucleic acid molecule that is added, either to the extraction step or to the PCR step, in a known concentration. The concept of adding an exogenous nucleic acid at a known concentration in order to act as an internal standard for quantitation was introduced by Chelly et al. (1988) Nature 333: 858-860, which is specifically incorporated herein by reference. Therefore, utilizing a control fragment that is amplified with the same primers as the target sequence more accurately reflects target sequence amplification efficiency relative to the internal standard (see, for example, WO 93/02215; WO 92/11273.; U.S. Pat. Nos. 5,213,961 and 5,219,727, all of which are incorporated herein by reference). Similar strategies have proven effective for quantitative measurement of nucleic acids utilizing isothermal amplification reactions such as NASBA (Kievits et al., 1991, J Virol Methods. 35:273-86) or SDA (Walker, 1994, Nucleic Acids Res. 22:2670-7).

The use of an endogenous control regulates variations in extraction efficiency. Control choice is important in that several requirements must be met in order for it to work. The first requirement is that the copy number of the control must remain constant; the second. Requirement is that the control must amplify with similar efficiency to the sequence being monitored. Several constitutively expressed genes have been considered as control candidates, since the expression of these genes is relatively constant over a variety of conditions. Examples include, but are not limited to, the β-actin gene, the glyceraldehyde-3-phosphate dehydrogenase gene (GAPDH), and the 16S ribosomal RNA gene. While these genes are considered to be constitutively expressed.

Threshold may be set up arbitrarily for the classification of differentially expressed polynucleotides. For example, a polynucleotide with a ratio of larger than 1.2 or less than 0.5 is regarded as a differentially expressed polynucleotide (i.e., gene) in the two samples according to one embodiment. Polynucleotides identified as differentially expressed can be collected, e.g., by a fraction collector, and the identity of the gene can be established through routine DNA sequencing. Fraction collectors are commercially available, for example, from Bio-Rad Laboratories (Hercules, Calif.).

In another embodiment, since the CE can be calibrated for determining molecular weights of eluted PCR fragments, and since the exact sequence used to selectively synthesize the second strand cDNA is known, the identity of each PCR fragment of interest can be readily determined based on the available genome sequence database information. The human genome has been completely sequenced, so are a few other organisms such as *E. coli*, yeast, *C. elegan* and *Drosophila*. With the fast advancement in DNA sequencing technology, the whole genomes of most other organisms of interest will soon completely sequenced.

One of the unique features of this method of transcription profiling is its ability to monitor PCR throughout the entire amplification process. In contrast, existing methods such as differential display only measure final quantities of PCR products. The advantage of this method is that it can detect those changes in gene expression that would otherwise be missed using other conventional methods. This aspect can be illustrated by the typical curves of PCR product accumulation (see FIG. 5).

At the beginning of the PCR amplification reaction, the amount of PCR product is below the detection limit of most instruments and no quantitative difference can be observed. For the detection of rare gene transcripts which are normally present, at the level of several copies per cell, monitoring PCR products at very late stages will be necessary. Typically, detection of these genes will be difficult since the reaction is typically stopped long before those rare transcripts are amplified to a detectable level. The middle section of the amplification curve, when the signal arises above the detection limit and enters a logarithmic phase, constitutes the best signal for detecting quantitative differences in gene expression. However, due to the exponential nature of the reaction, this phase is relatively short and lasts only a few cycles before the reaction goes into a later stationary phase. In this later stationary phase of PCR amplification, accumulation of PCR products are saturated due to several factors such as lack of additional substrates, or lack of polymerase, or inhibition of polymerase activity by the product, or a combination thereof. Obviously, this later stationary phase once again provides little opportunity for detecting quantitative differences in gene expression. Therefore, methods that quantify PCR product after a predetermined number of cycles can only identify genes that happens to be in the logarithmic phase of the amplification and would thus miss those genes which are only differentially detected either earlier or later in the amplification process.

The instant invention overcomes this limitation since it defines a complete amplification curve for each individual amplified fragment. Moreover, it provides a quantitative basis for measuring expression differences. In the practice of real time quantitative PCR, the experimentally defined parameter $C_t$. As used herein, the term "$C_t$" refers to the cycle number at which the signal generated from a quantitative PCR reaction first rises above a "threshold", i.e., where there is the first reliable detection of amplification of a target nucleic acid sequence. "Reliable" means that the signal reflects a detectable level of amplified product during PCR. $C_t$ generally correlates with starting quantity of an unknown amount of a target nucleic acid, e.g., lower amounts of target result in later $C_t$. Ct is linked to the initial copy number or concentration of starting DNA by a simple mathematical equation:

Log(copy number)=$aC_t$+b, where a and b are constants.

Therefore, by measuring $C_t$ for the fragments of the same gene originating from two different samples, the original concentration of this gene in these samples can be easily evaluated.

The usual source of concerns regarding the use of PCR amplification for expression profiling is a potential bias of amplification. Specifically, some sequences are amplified with a better efficiency than others. This bias can change the final representation of PCR products when compared with the starting sample. However, such bias will not affect the instant invention because the invention provides an embodiment where amplification of a cDNA target from different samples is performed in the same reaction mixture and with the use of a common PCR primer. Therefore the ratio of the amplified PCR product originating from different samples will only be affected by the ratio of original amount of cDNA in each sample but not by the efficiency of amplification. For a given PCR reaction, although amplification of one PCR target may still be biased against another, this ratio shall remain constant without regard to the size or the composition of each PCR product. Thus, this method provides an embodiment which bypasses such problem by measuring relative, instead of absolute, amplification of two samples in the same PCR reaction.

Other potential problems can arise late in the amplification when availability of DNA polymerase may became a limiting factor of amplification. As a consequence, more abundant fragments will kinetically inhibit amplification of less abundant fragments. The importance of this problem cannot be empirically predicted since it depends on the sensitivity of the detection device. One way to alleviate the problem is to gradually increase concentration of the DNA polymerase at the late cycles of amplification.

Figure 6:
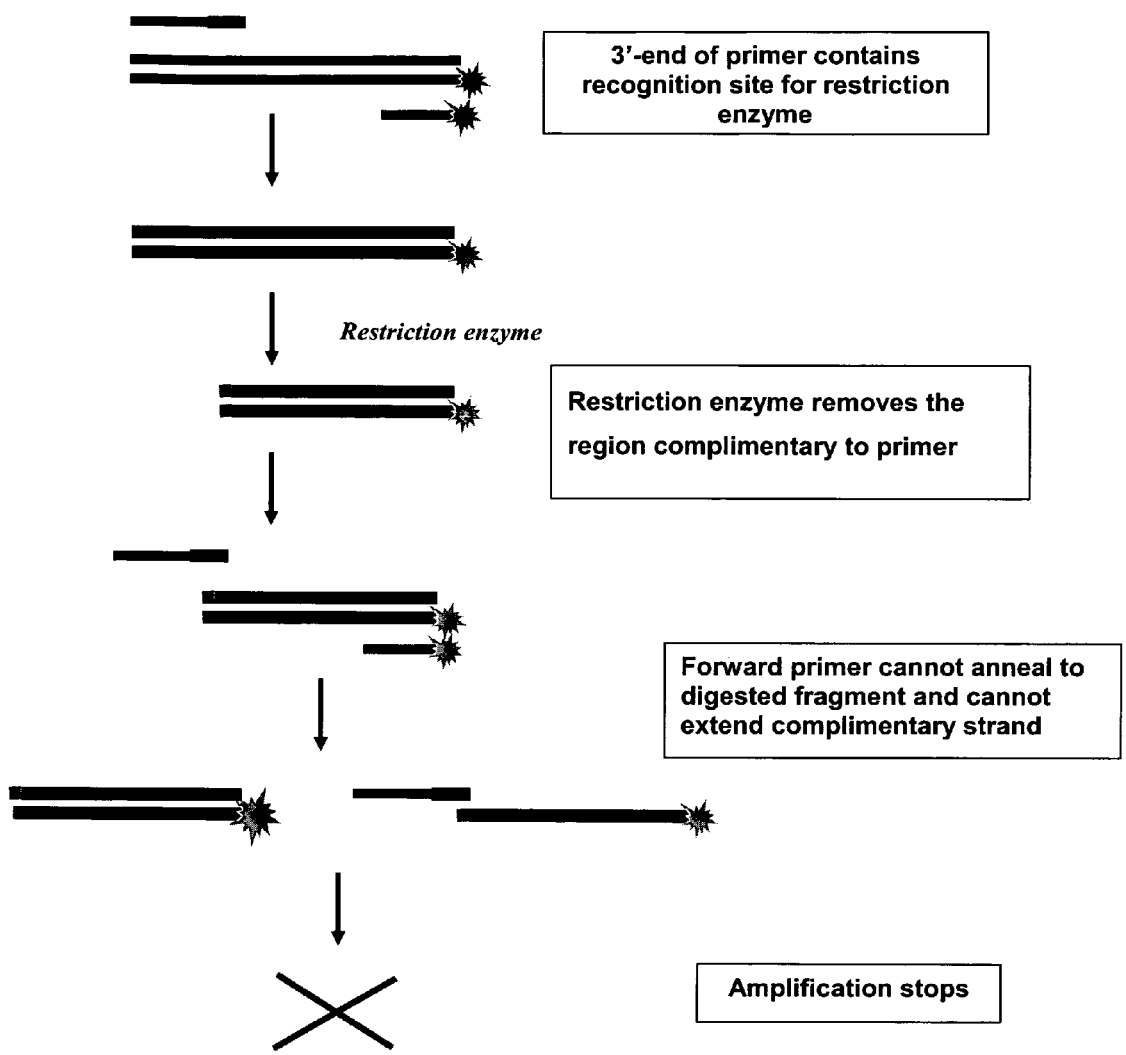
FIG. 6 is a diagram showing the normalized PCR Amplification scheme according to one embodiment of the invention.

Another method to address the issue of kinetic bias of the PCR is a novel concept (normalized amplification or amplification to steady-state). In one embodiment, we propose to include additional step in each cycle of amplification starting with cycles 10-20. This step consists of treating the amplification mixture with the restriction enzyme directed against the palindromic sequence included in the primers 2 (FIG. 6). The more abundant PCR fragments will be preferentially digested by the restriction enzyme simply due to their relative abundance. The digestion will eliminate a priming site for the DNA polymerase and therefore will prevent further amplification of digested fragments. Undigested PCR fragments, which include less abundant DNA fragments will continue to amplify, generating 2 copies of each fragment in the reaction. By adjusting the concentration of the restriction enzyme and the time of this treatment it should be possible to regulate this reaction in such way that it will limit further amplification of the PCR fragments after they will reach certain acceptable concentration. To eliminate the difference in the size between digested and undigested fragments corresponding to the same gene, the aliquot of the reaction mixture will be treated with an excessive amount of the restriction enzyme. Likewise, single-stranded DNA species arising from the priming of the opposite strand of DNA could be eliminated by the treatment with the single-stranded DNases (for example Exonucleases I and VII).

The above description is directed to an embodiment that measures differences between two original samples. However, it should be understood that more than two samples could also be used in the same manner as described with minor adaptation. For example, by using a third sample-specific primer and a third fluorescent label, the same method can be used for three samples. Similarly, even more samples can also be analyzed using a similar approach.

Kits for Implementing the Method of the Invention

The invention includes compositions and kits for carrying out the various embodiments of the invention. Preferably, kits of the invention include a first oligonucleotide primer, where the first oligonucleotide primer comprises a sample-specific sequence tag and where the sample-specific sequence tag is GC rich at its 5' terminal and AT rich at its 3' terminal. Preferably, the first oligonucleotide is attached to a solid support. Additionally, kits of the invention may further include a second oligonucleotide primer, a third oligonucleotide primer, or a fourth oligonucleotide primer, where second oligonucleotide primer may comprise an arbitrary sequence tag. Kits may further contain one or more components selected from the group of a reverse transcriptase, a DNA polymerase, a reaction buffer, and dNTPs.

Exemplary Applications of the Present Methods

1. Research on Development and Signal Transduction Pathways

Comparing expression profiles of different biological samples are invaluable for studying normal developmental processes.

For example, stem cell differentiation is characterized by a series of specialization into stem cells that are committed to give rise to cells that have a particular function. Totipotent embryonic stem cells may partially differentiate into pluripotent stem cells, which in turn may give rise to blood stem cells under certain conditions. These committed blood stem cells will respond to a host of cytokines or "stimulating factors" en route to their further differentiation into more specialized blood bells such as red blood cells, platelets, and white blood cells. During each step of this complicated process, dramatic changes in overall gene expression profiles occur in response to particular cytokines. It is of great interest to determine what are the governing factors for these kind of fate determination during stem cell differentiation since a partial or complete reversion of these steps may be beneficial in regaining some desirable features that are lost during differentiation. Similar approaches may be desirable for a number of other developmental processes. The instant invention provides a tool to study such changes in gene expression profile during development and thus will be of great value for such research.

2. Therapeutic Uses and Diagnostic Markers

The instant invention provides a method to compare expression profiles of different biological samples, which offers an invaluable means to identify potential drug targets for further research and development and useful diagnostic markers for certain pathological conditions.

There are at least two types of genes which expression profiles may be changed in diseased vs. normal samples. Change in expression profile of one type of genes is causally related the disease state. It is the up- or down-regulation of these genes that trigger a series of events that eventually leads to the development of the pathological condition. By modulating the activity of these "causal genes," it is possible to reverse the disease state and therefore effective treat or alleviate the pathological condition. These genes and their products constitute valuable drug targets, the mere identification of which will be beneficial for the long term goal of curing the disease. Examples of such genes will include, but are not limited to oncogenes (such as Ras) and tumor suppressor genes (such as Rb, NF1).

The second type of genes which expression profiles are changed are different in that these changes are the result rather than the cause of such disease conditions. Although it may not be possible to modulate the activity of these genes in the hope that the disease phenotype will be reversed, identification of these genes may nevertheless help early accurate diagnosis of such disease conditions, thereby facilitating early and effective treatment of such conditions. Examples of such genes will include but are not limited to tumor antigens CA125, alpha fetal protein, etc.

In addition, the instant invention can also be employed to study the effects of certain treatments on cells, tissues or individual. This is useful for basic and pharmaceutical research when the effect of a potential drug can be studied and/or predicted based on what signal transduction pathways are affected by certain treatments. By identifying the potential target of such drug, certain undesirable side effects might be eliminated by further screening for better drugs that only affects desired targets while leaving other unintended targets alone. Drug optimization is also possible since the instant invention provides a means to do high throughput screen to identify improved drugs that causes larger desirable changes in the intended target.

3. Other Applications

Another area where a simple method of transcriptional profiling can be extremely instrumental is characterization of cells and organisms that underwent genetic modifications (for example transgenic animals carrying a modified version of the gene, overexpressing genes or missing genes (knockouts)). Such cells and organisms often display an altered transcription profile as a result of the modified function of the targeted gene or as a compensating effect. Such changes can point out to the function of the gene by placing it to the particular pathway defined by the identity of the differentially expressed genes. It may help to define a transcriptional signature of alteration in particular genes and to use such signatures to define genetic modification in a particular disease by comparison of the transcriptional changes in cells or tissues obtained from the disease-affected organisms versus a database of transcriptional signatures.

4. Business Methods

The instant invention also provides a business method to conduct a pharmaceutical business. Identification and validation of drug targets are important rate limiting steps in the drug development process. The instant invention provides a method to quickly compare the expression profiles of diseased vs. normal tissues, thereby significantly speed up the process of identifying potential lead molecules for drug design. The associated high throughput means will also help to speed up the drug screening as well as drug optimization processes. In addition, a number of reliable diagnostic markers can be identified and further developed for diagnosis purpose. This will not only provide a basis for a pharmaceutical business to carry out the identification and development of these drug targets or markers, but also an opportunity to license the rights of these initial discoveries to a third party so that they can conduct further research and development of the target of their choice. In addition, it is also possible to offer the service of identifying and developing such drug targets or markers using proprietary technology of the instant invention.

The instant invention has the potential to become a powerful tool for transcriptional profiling as a new platform for genomic discovery. This system has a potential for improvements and further development (e.g. increasing number of samples, creation of the band ID database eliminating the need for sequencing, etc.). It will also speed up the whole process of DNA diagnostics (in particular development of low and medium-density microarrays) by providing the initial data to select specific sets of genes for down-stream applications.

The practice of the present invention will employ, unless otherwise indicated, conventional techniques of molecular biology, cell biology, cell culture, microbiology and recombinant DNA, which are within the skill of the art. Such techniques are explained fully in the literature. See, for example, *Molecular Cloning: A Laboratory Manual,* 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al.; U.S. Pat. No. 4,683,195; *Polynucleotide Hybridization* (B. D. Hames & S. J. Higgins eds., 1984); *Transcription And Translation* (B. D. Hames & S. J. Higgins eds., 1984); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.); *Immunochemical Methods In Cell And Molecular Biology* (Mayer & Walker eds., Academic Press, London, 1987). The contents of all cited references (including literature references, issued patents, published patent applications as cited throughout this application) are hereby expressly incorporated by reference.

In particular, isolation of total RNA from biological samples and subsequent purification of mRNA for cDNA synthesis is well known molecular biology techniques. The details of experimental procedures are well documented in one or more laboratory reference books listed above and other scientific literatures. Commercial kits are also widely available for such purposes (for example, Qiagen sells kits for mRNA isolation and GIBCO BRL sells kits for cDNA synthesis using reverse transcriptase). PCR amplification, chromatography, capillary electrophoresis (CE) are all routine molecular biology techniques and thus will not be elaborated further.

EXAMPLES

The invention is illustrated by the following nonlimiting examples wherein the following materials and methods are employed.

Example 1

Preparation of RNA

RNA may be produced using Trizol reagent and RNeasy Midi/Maxi Kit from Qiagen by following the following procedure.

Tissues were homogenized in a homogenizer at 1 ml of TRIZOL reagent per 50-100 mg of tissue for 30 seconds, followed by a final homogenization of 1 minute. The sample volume should not exceed 10% of the volume of Trizol reagent used for homogenization. The homogenized tissues were left for at least 15 minutes up to an hour, at room temperature, or they were stored in −70° C. until needed. 0.2 ml of chloroform per ml of Trizol was added and mixed by shaking. The mixture was incubated at room temperature for 5 minutes, then centrifuged for 5 minutes at 4000 rpm. The upper phase was collected into a separate tube. 0.5 ml of isopropyl alcohol per ml of Trizol was added to precipitate RNA. The mixture was put on ice for 5 minutes and was centrifuged at 4000 rpm for 10 minutes. The supernatant was removed and the pellet was washed with 1 ml 75% EtOH per ml of Trizol, mixed, and centrifuged at 4000 rpm for 5 minutes. The supernatant was moved and the pellet was air dried for 30 minutes to 1 hour. After pellet was air dried, the pellet was resuspended in RNAse free water to a desired concentration.

The RNA extracted could be cleaned up by adding the appropriate volume of buffer RLT, and mix thoroughly. An appropriate volume of ethanol (96-100%) was added to the diluted RNA and mixed thoroughly by shaking vigorously. The sample was applied to an RNeasy midi spin column or RNeasy maxi spin column and was placed in a 15-ml or 50-ml centrifuge tube and centrifuge for 5 min at 3000-5000×g. The flow-through was discarded.

Generally, DNase digestion is not required since the RNeasy silica-membrane technology efficiently removes most of the DNA without DNase treatment. However, further DNA removal may be necessary for certain RNA applications that are sensitive to very small amounts of DNA. To remove DNA with DNase, pipet 2.0 ml buffer RW1 into spin column and centrifuge for 5 minutes at 3000-5000×g to wash. Discard the flow through and reuse the centrifuge tube. Add 20 µl DNase 1 stock solution to 140 µl buffer RDD. Mix by gently flicking the tube, and centrifuge briefly to collect residual liquid from the sides of the tube. Pipet the DNase 1 incubation mix (160 µl) directly onto the spin column membrane, and place on the benchtop (20-30 □C) for 15 min. Pipet 2.0 ml RW1 buffer into the spin column, and place on the benchtop for 5 min. Then centrifuge for 5 minutes at 3000-5000×g. Discard the flow through. Reuse the centrifuge tube in the following RPE buffer wash step. RNeasy kit is used for remainder of protocol by following the manufacturer's manual instruction.

Example 2

Reverse Transcription in Solution

The RNA samples (1-5 µl) were mixed with 1 µl of dNTPs solution (10 mM) and 0.0005-0.5 µM (final concentration in 20 µl mixture) of first oligonucleotide, heated for 7 min at 70° C., cooled for 2 min at 4° C. The above mixture was then mixed with the reaction mixture (4 µl RT buffer (250 mM Tris-HCl (pH 8.3 at 25° C.), 375 mM KCl, 15 mM MgCl$_2$), 2 µl 0.1 M DTT, 1 µl RNAse inhibitor (Ambion) and 1 µl of SuperScriptII reverse transcriptase (Invitrogen) and 5-10 µl of water) in a total volume of 20 µl. The reverse transcription reaction was incubated for 1-2 hours at 45° C. and was terminated by heating at 65° C. for 10 min. An aliquot of sample (5-20 µl) was directly analyzed by PCR. Optionally, the RNA templates were degraded by incubation with RNAse H enzyme (Invitrogen) prior to PCR amplification.

Example 3

Reverse Transcription on Beads a. Coupling of Oligonucleotides to Beads

Ultralink™ Iodoacetyl beads (Pierce) (100-1000 µl) were washed 4 times with 5×TE buffer (50 mM Tris, 5 mM EDTA, pH 8.0) and mixed with the solution of thiolated (5' thiol) oligonucleotide (1-10 µM). The coupling reaction was initiated by addition of the reducing agent TCEP (Tris(2-carboxyethyl) phosphine) (100-500 µM) and conducted for 1-2 hours at room temperature with continued mixing. The unreacted active groups on the beads were quenched by addition of 1% of beta mercaptoethanol for 10 min. Oligo-beads were washed consequentially with 10 volumes each of 4 times 5×TE buffer, 2 times 5×TE buffer at 75° C., 2 times RT buffer at 85° C., 2×RT buffer and RT buffer at 95° C. The prepared beads were kept at 4° C. in RT buffer.

b. Reverse Transcription

The RNA samples (1-5 µl) were mixed with 1 µl of dNTPs solution (10 mM) and 6-10 µl of oligo-beads, heated for 7 min at 70° C., cooled for 2 min at 4° C. and mixed with the reaction mixture (4 µl RT buffer (250 mM Tris-HCl (pH 8.3 at 25° C.), 375 mM KCl, 15 mM MgCl$_2$), 2 µl 0.1 M DTT, 1 µl RNAse inhibitor (Ambion) and 1 µl of SuperScriptII reverse transcriptase (Invitrogen) and 0-4 µl of water). The reverse transcription reaction was incubated for 1-2 hours at 45° C. The reaction was terminated by heating at 65° C. for 10 min. The beads were washed twice with PCR buffer. RNA templates were destroyed by incubation with RNAse H enzyme (Invitrogen) or alkaline hydrolysis. The latter reaction was carried out by addition of 3.5 µl of 0.5 M NaOH to the reaction mixture, incubation for 5 min at 65° C. and neutralized with 3.5 µl of 1 M Tris pH 7.5. The beads were washed twice with PCR buffer.

Example 4

Second Strand Synthesis

The synthesis of the second strand of bound DNA was performed with mixture of Taq polymerase (Hot-start Taq, Qiagen) (0.5-1.5 u) and Pwo DNA polymerase (Roche) (0.25-0.5 u) in PCR thermocycler programmed for 30 s at 95° C., 30 s at 56° C. and 2 min at 72° C.). The reaction mixture included 6-10 µl of cDNA on oligobeads from RT reaction, 5 µl of 10×PCR buffer (Hot-start Taq, Qiagen) or 10×RT-PCR buffer (500 mM Tris, 200 mM KCl, 100 mM (NH$_4$)$_2$SO$_4$, 2.5 mM Mg$_2$Cl, pH 8.5), 0.1 mM dNTPs, 0.5-1 µl of second primer (100 µM) in a total volume of 50 µl. The synthesized second DNA strand was removed from the beads at 96° C. and used for further amplification.

Alternatively second strand DNA was synthesized using DNA polymerase 1 or it Klenow fragment in the presence of 50 mM Tris pH 7.5, 10 mM Mg Cl$_2$ 1 mM DTT, and 0.05 mg/ml BSA, 0.1 mM dNTP, 7 mM MgCl$_2$ and 1 µM of second primer for 30 min at 37° C. The synthesized second DNA strand was removed as described above.

Example 5

PCR Amplification

PCR amplification of synthesized cDNA (5-20 µl) was amplified in the presence of 10 µl of 10×PCR buffer or 10× RT-PCR buffer (see above), 2-3 mM MgCl$_2$, 0.05-0.2 mM dNTPs, 0.1-1 µM of third primers labeled with either FAM, Rox, or Hex, 0-1 µM of unlabeled third primers, 1-2 µl of fourth primer, 0-5% DMSO, 0.5-2 u of proofreading DNA polymerase (Pwo or Tgo (Roche)) and 1.5-3 u of hot-start DNA polymerase (e.g. Hot-Start Taq polymerase (Qiagen)). The amplification was conducted using "I-cycler" (BioRad) or "PCR Express" (Thermo Hybaid) thermocyclers using following cycling program: 95° C. for 30 s, 56-60° C. for 15-30° C., 72° C. for 1 min 30 sec for 30-40 cycles total.

Aliqouts of samples (typically 25 μl) were withdrawn after each cycle at the end of extension step (72° C.) starting with 10-15$^{th}$ cycle. Equal volume of PCR mix containing primers, polymerase and dNTPs was placed into reaction mix after each sample removal. The collected samples were analyzed using CE system from Spectrumedix (SCE-9610 Genetic Analysis System) or ABI (3700 Prism System).

Example 6

Capillary Electrophoresis

Capillary electrophoresis was performed on SCE 9610 fully automated 96-capillary electrophoresis genetic analysis system from Spectrumedix Corporation according to the manufacture's instruction.

OTHER EMBODIMENTS

The foregoing embodiments demonstrate experiments performed and techniques contemplated by the present inventors in making and carrying out the invention. It is believed that these embodiments include a disclosure of techniques which serve to both apprise the art of the practice of the invention and to demonstrate its usefulness. It will be appreciated by those of skill in the art that the techniques and embodiments disclosed herein are preferred embodiments only that in general numerous equivalent methods and techniques may be employed to achieve the same result.

All of the references identified hereinabove, are hereby expressly incorporated by reference in their entirety.

The invention claimed is:

1. A method for comparing gene expression profiles of two or more samples, said method comprising:
(a) synthesizing a plurality of first strand cDNAs from a first sample using a mixture of first-strand primers comprising [5'-(sample-specific sequence tag A)$_{20-24}$T$_{12-16}$AN-3', 5'-(sample-specific sequence tag A)$_{20-24}$T$_{12-16}$CN-3', and 5'-(sample-specific sequence tag A)$_{20-24}$T$_{12-16}$GN-3'], wherein N is any of G, A, T or C;
(b) synthesizing a plurality of first strand cDNAs from a second sample using a mixture of first-strand primers comprising [5'-(sample-specific sequence tag B)$_{20-24}$T$_{12-16}$AN-3', 5'-(sample-specific sequence tag B)$_{20-24}$T$_{12-16}$CN-3', and 5'-(sample-specific sequence tag B)$_{20-24}$T$_{12-16}$GN-3'], wherein N is any of G, A, T, or C and wherein said sample-specific sequence tag A is different from said sample-specific tag B;
(c) mixing first-strand cDNAs from said first sample with first-strand cDNAs from said second sample to form a single reaction mixture;
(d) co-amplifying said cDNAs in said reaction mixture of step (c) using a mixture of primers comprising a primer common to both samples, a primer specific for said sequence tag A, and a primer specific for said sequence tag B, wherein said co-amplifying permits selectively amplifying at least a subset of said cDNA so as to generate one or more sample-specific amplified products;
(e) detecting the abundance of one or more said sample-specific amplified products, wherein said abundance determines an expression profile of one or more genes in said first and said second sample; and
(f) comparing the expression profile of said one or more genes in said first sample with an expression profile of said one or more genes in said second sample, wherein a difference in the expression profile indicates differential expression of said one or more genes in said first and second samples.

2. The method of claim 1, wherein said sample-specific sequence tags A and B are each 15-30 nucleotides in length.

3. The method of claim 1, wherein said sample-specific sequence tags A and B are each 20-24 nucleotides in length.

4. The method of claim 1, wherein said first-strand primer further comprises a sequence of 5' oligo(dT)$_n$VN 3', where n is at least 5; V is dATP, dGTP, or dCTP; and N is dTTP (or dUTP), dATP, dGTP, or dCTP.

5. The method of claim 4, wherein in said first-strand primer, said sample-specific sequence tag A or B is located at the 5' of oligo(dT)$_n$VN.

6. The method of claim 1, wherein said first-strand primer is linked to a detectable label.

7. The method of claim 6, wherein said detectable label is a fluorescent label.

8. The method of claim 6, wherein said first-strand primer used for each of two or more samples is labeled with a sample-specific label.

9. The method of claim 1, wherein said one or more amplified products are sampled at a predetermined time or cycle interval during the amplification.

10. The method of claim 9, wherein the abundance is detected for each sampled amplified product.

11. The method of claim 1, wherein said method further comprises separating said one or more amplified products before detecting the abundance of said one or more amplified products.

12. The method of claim 11, wherein said one or more amplified products are separated and their abundance detected by measurement of fluorescence.

13. The method of claim 11, wherein said one or more amplified products are separated by electrophoresis.

14. The method of claim 13, wherein said one or more amplified products are separated by capillary electrophoresis.

15. The method of claim 1, wherein said method further comprises generating an amplification plot, calculating a Ct of amplification for each of said one or more genes, and measuring the difference in the expression profile by a ratio of said Cts.

16. A method for comparing gene expression profiles of two or more samples, said method comprising:
(a) synthesizing a plurality of first strand cDNAs from a first sample using a first oligonucleotide primer comprising a first sample-specific sequence tag, and synthesizing a plurality of first strand cDNAs from a second sample using a second oligonucleotide primer comprising a second, distinct sample-specific sequence tag, wherein said first and said second oligonucleotide primer each comprise at least one degenerate nucleotide;
(b) mixing said plurality of first strand cDNAs from said first and said second sample into a single reaction mixture and co-amplifying said cDNAs using a mixture of primers comprising a primer common to both samples, a primer specific for said first sample-specific sequence tag, and a primer specific for said second sample-specific sequence tag, wherein said co-amplifying permits selectively amplifying at least a subset of said cDNA so as to generate one or more sample-specific amplified products;
(c) detecting the abundance of one or more said sample-specific amplified products, wherein said abundance determines an expression profile of one or more genes in said first and said second sample; and (d) comparing the expression profile of said one or more genes in said first sample with an expression profile of said one or more genes in said second sample, wherein a difference in the expression profile indicates differential expression of said one or more genes in the two samples.

17. A method for comparing gene expression profiles of two or more samples, said method comprising:
(a) synthesizing a plurality of first strand cDNAs from a first sample using a first oligonucleotide primer comprising a first sample-specific sequence tag, and synthesizing a plurality of first strand cDNAs from a second sample using a second oligonucleotide primer, comprising a second, distinct sample-specific sequence tag wherein each of said sample specific sequence tags comprise at least one artificial nucleotide;
(b) mixing said plurality of first strand cDNAs from said first and said second sample into a single reaction mixture and co-amplifying said cDNAs using a mixture of primers comprising a primer common to both samples, a primer specific for said first sample-specific sequence tag, and a primer specific for said second sample-specific sequence tag, wherein said co-amplifying permits selectively amplifying at least a subset of said cDNA so as to generate one or more sample-specific amplified products;
(c) detecting the abundance of one or more said sample-specific amplified products, wherein said abundance determines an expression profile of one or more genes in said first and said second sample; and
(d) comparing the expression profile of said one or more genes in said first sample with an expression profile of said one or more genes in said second sample, wherein a difference in the expression profile indicates differential expression of said one or more genes in the two samples.

18. A method for comparing gene expression profiles of two or more samples, said method comprising:
(a) synthesizing a plurality of first strand cDNAs from a first sample using a first oligonucleotide primer comprising a first sample-specific sequence tag, and synthesizing a plurality of first strand cDNAs from a second sample using a second oligonucleotide primer comprising a second, distinct sample-specific sequence tag;
(b) mixing said plurality of first strand cDNAs from said first and said second sample into a single reaction and co-amplifying said cDNAs using a mixture of primers comprising a primer common to both samples, a primer specific for said first sample-specific sequence tag, and a primer specific for said second sample-specific sequence tag, wherein said co-amplifying permits selectively amplifying at least a subset of said cDNA so as to generate one or more sample-specific amplified products;
(c) detecting the abundance of one or more said sample-specific amplified products, wherein said abundance determines an expression profile of one or more genes in said first and said second sample; and
(d) comparing the expression profile of said one or more genes in said first sample with an expression profile of said one or more genes in said second sample, wherein a difference in the expression profile indicates differential expression of said one or more genes in the two samples.

19. The method of claim 18 wherein said primer common to both samples comprises a 6-25 nucleotide randomly selected sequence at its 3' end.

20. The method of claim 18 wherein said primer common to both samples comprises a 6-7 nucleotide randomly selected sequence at its 3' end.

* * * * *